(12) United States Patent
Keyaki et al.

(10) Patent No.: US 12,430,823 B2
(45) Date of Patent: *Sep. 30, 2025

(54) X-RAY CT APPARATUS AND RECONSTRUCTION METHOD OF TOMOGRAPHIC IMAGE

(71) Applicant: Shimadzu Corporation, Kyoto (JP)

(72) Inventors: Yasuyuki Keyaki, Kyoto (JP); Ryo Takahashi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 276 days.

This patent is subject to a terminal disclaimer.

(21) Appl. No.: 18/313,579

(22) Filed: May 8, 2023

(65) Prior Publication Data
US 2023/0368440 A1    Nov. 16, 2023

(30) Foreign Application Priority Data
May 13, 2022  (JP) .................................. 2022-079781

(51) Int. Cl.
*A61B 6/46*    (2024.01)
*A61B 6/03*    (2006.01)
*G06T 11/00*   (2006.01)

(52) U.S. Cl.
CPC ............ *G06T 11/006* (2013.01); *A61B 6/032* (2013.01); *A61B 6/463* (2013.01); *A61B 6/465* (2013.01); *A61B 6/469* (2013.01)

(58) Field of Classification Search
CPC ....... G06T 11/006; A61B 6/032; A61B 6/463; A61B 6/465; A61B 6/469; A61B 6/5205; A61B 6/545
See application file for complete search history.

(56) References Cited

U.S. PATENT DOCUMENTS

2012/0140874 A1*  6/2012  Li .......................... A61B 6/032
                                                                 378/11
2023/0368439 A1* 11/2023  Keyaki .................. A61B 6/545

FOREIGN PATENT DOCUMENTS

WO    2017169232 A1    10/2017

* cited by examiner

*Primary Examiner* — Courtney D Thomas
(74) *Attorney, Agent, or Firm* — Maier & Maier, PLLC

(57) ABSTRACT

In an X-ray CT apparatus, a processor is configured to display, on a display device, an X-ray projection image based on projection data, and perform processing of displaying a GUI, which is a graphical user interface for setting or adjusting a region of interest in a rotation axis direction of a subject for which a tomographic image is reconstructed, in region-of-interest reconstruction processing.

11 Claims, 14 Drawing Sheets

X-RAY CT APPARATUS AND RECONSTRUCTION METHOD OF TOMOGRAPHIC IMAGE

CROSS-REFERENCE TO RELATED APPLICATIONS

The related application number JP2022-079781, an X-ray CT apparatus and a reconstruction method of a tomographic image, May 13, 2022, Yasuyuki Keyaki and Ryo Takahashi upon which this patent application is based are hereby incorporated by reference.

FIELD

The present invention relates to an X-ray CT apparatus and a reconstruction method of a tomographic image.

BACKGROUND

In imaging with an X-ray CT apparatus, in a case in which a magnification ratio is increased and a part of a subject is imaged, projection data is acquired while rotating the subject in a state in which a part of the subject is included in an X-ray irradiation region and the other part protrudes from the X-ray irradiation region. In such a case, in a case in which a tomographic image is constructed, there is an inconvenience that an artifact (noise) is generated at a boundary between the part of the subject in the X-ray irradiation region and the protruding part of the subject due to information contradiction of the protruding part of the subject.

In order to solve such an inconvenience, in the reconstruction of the tomographic image using the X-ray CT apparatus, the use of the reconstruction method of the tomographic image of executing the Hilbert transformation to reconstruct the tomographic image of the subject in a region of interest is under consideration. Such a reconstruction method of the tomographic image is disclosed, for example, in Pamphlet of International Publication WO. 2017/169232. In the reconstruction method of the tomographic image, projection data transmitted through the subject in the region of interest is processed by the Hilbert transformation to reconstruct the tomographic image of the subject in the region of interest.

However, in the reconstruction method of the tomographic image as disclosed in Pamphlet of International Publication WO. 2017/169232, although not disclosed in Pamphlet of International Publication WO. 2017/169232, there is a case in which the artifact (noise) is generated at a location having a large change in the projection data in a rotation axis direction of the subject, such as a boundary between a region of the subject and a region without the subject. Therefore, in order to suppress the generation of the artifact (noise), it is necessary to appropriately set or adjust the region of interest in the rotation axis direction of the subject depending on the subject. That is, in a case in which the tomographic image in the region of interest is reconstructed by using the reconstruction method of the tomographic image as disclosed in Pamphlet of International Publication WO. 2017/169232, in a case in which a position of the subject in the rotation axis direction is not accurately grasped when the region of interest in the rotation axis direction of the subject is set or adjusted, the user cannot appropriately and easily set or adjust a Hilbert transformation region. Therefore, there is a demand for an X-ray CT apparatus and a reconstruction method of a tomographic image which can appropriately and easily set or adjust the region of interest in the rotation axis direction of the subject depending on the subject.

SUMMARY

The present invention has been made to solve the above problems, and the present invention is to provide an X-ray CT apparatus and a reconstruction method of a tomographic image which can appropriately and easily set or adjust a region of interest in a rotation axis direction of a subject depending on the subject.

A first aspect of the present invention relates to an X-ray CT apparatus including an X-ray irradiator configured to emit X-rays, an X-ray detector configured to detect the X-rays emitted from the X-ray irradiator and transmitted through a subject, and a processor configured to perform tomographic image construction processing of constructing a tomographic image of the subject based on projection data acquired by irradiating the subject with the X-rays from a plurality of angles while rotating the subject, and perform region-of-interest reconstruction processing of reconstructing the tomographic image of the subject in a region of interest by executing Hilbert transformation, in which the processor is configured to display, on a display device, an X-ray projection image based on the projection data, and perform processing of displaying a GUI, which is a graphical user interface for setting or adjusting the region of interest in a rotation axis direction of the subject for which the tomographic image is reconstructed, in the region-of-interest reconstruction processing. It should be noted that the GUI, which is the graphical user interface, is used by a user to visually perceive and perform a command with respect to a computer on a screen. The GUI is a broad concept that includes an icon and a button for inputting the command with respect to the computer, a widget, such as a window and a text box, display (image) for notifying the user of information, and the like.

A second aspect of the present invention relates to a reconstruction method of a tomographic image, the method including a tomographic image construction processing step of performing tomographic image construction processing of constructing a tomographic image of a subject based on projection data acquired by irradiating the subject with X-rays from a plurality of angles, a projection image display step of displaying an X-ray projection image based on the projection data, a GUI display step of displaying a GUI, which is a graphical user interface for setting or adjusting a region of interest in a rotation axis direction of the subject for which the tomographic image is reconstructed, in region-of-interest reconstruction processing of reconstructing the tomographic image of the subject in the region of interest by executing Hilbert transformation, and a region-of-interest reconstruction processing step of performing the region-of-interest reconstruction processing based on the region of interest in the rotation axis direction of the subject which has been set or adjusted by using the GUI.

With the X-ray CT apparatus according to the first aspect of the present invention and the reconstruction method of the tomographic image according to the second aspect of the present invention, the X-ray projection image based on the projection data is displayed, and the GUI for setting or adjusting the region of interest in the rotation axis direction of the subject is also displayed, so that the user can appropriately set or adjust the region of interest in the rotation axis direction of the subject by using the GUI while visually recognizing the X-ray projection image based on the projection data of the subject and accurately grasping the position of the subject in the rotation axis direction. As a result, it is possible to provide the X-ray CT apparatus and the reconstruction method of the tomographic image which can appropriately and easily set or adjust the region of interest in the rotation axis direction of the subject depending on the subject.

DETAILED DESCRIPTION

Hereinafter, an embodiment embodying the present invention will be described with reference to the drawings.

Figure 1:
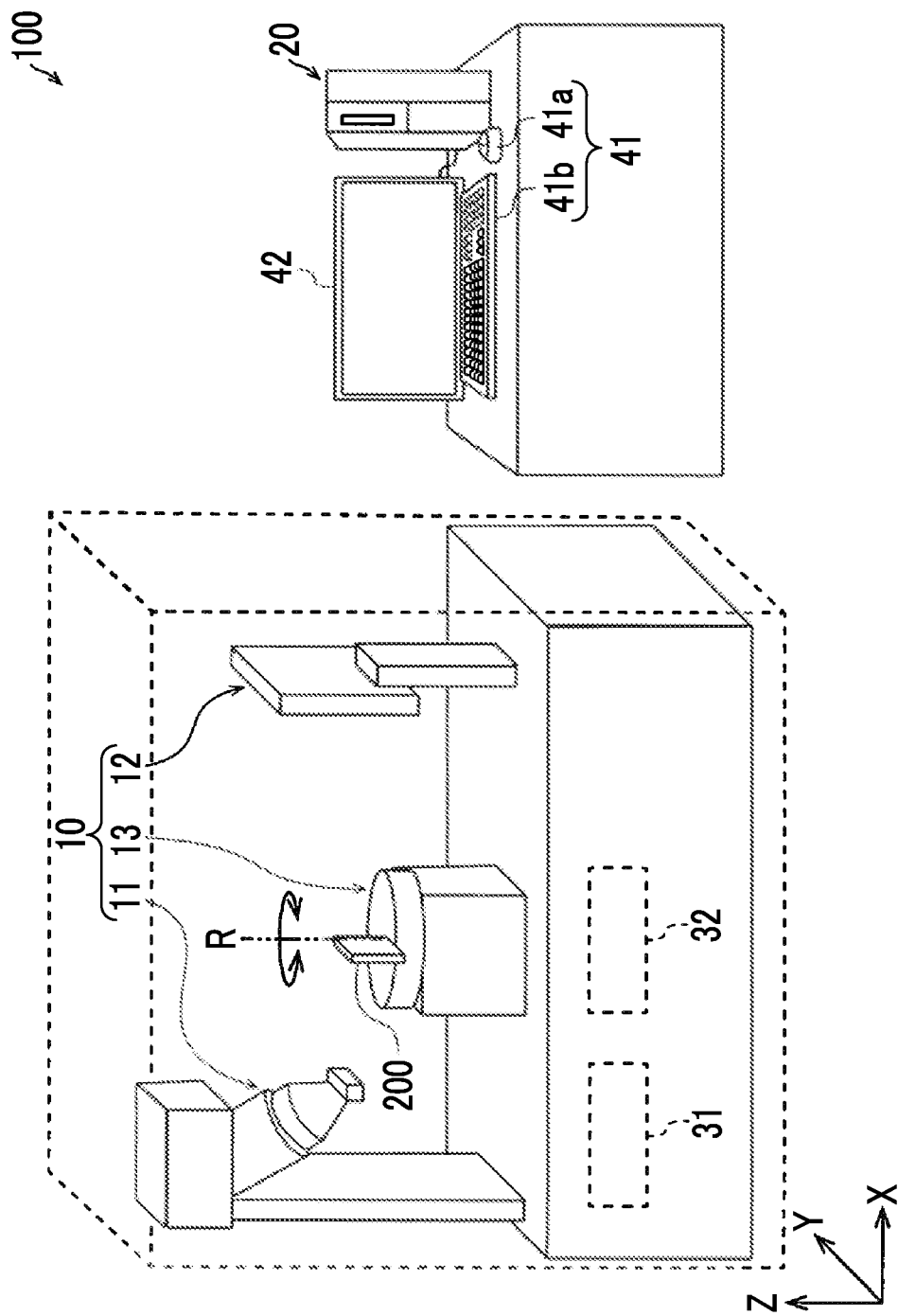
FIG. 1 is a schematic diagram showing an overall configuration of an X-ray CT apparatus according to an embodiment of the present invention.
Figure 7:
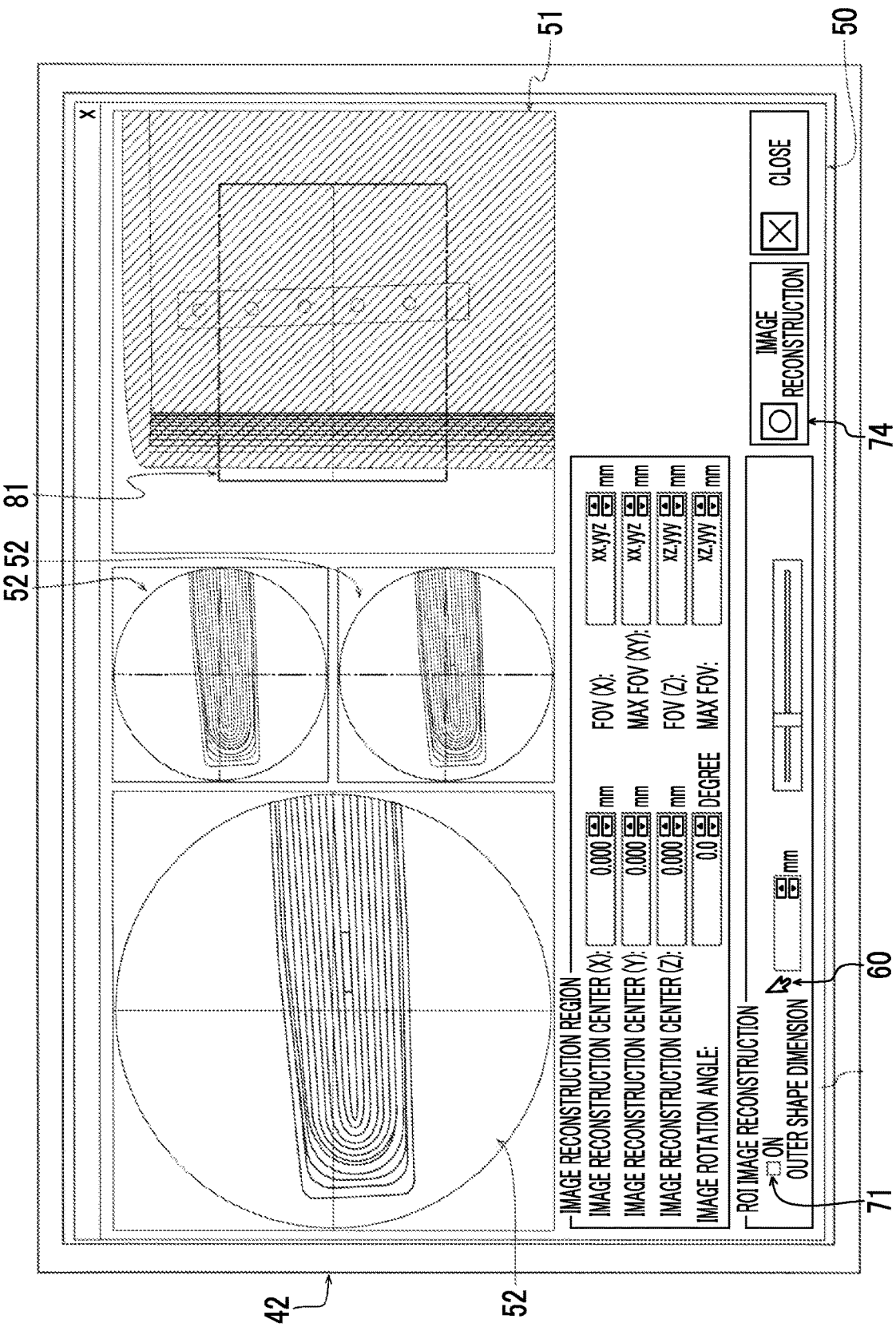
FIG. 7 is a diagram showing a GUI and a tomographic image displayed on a display device.

As shown in FIG. 1, an X-ray CT apparatus 100 is an industrial X-ray CT apparatus. The X-ray CT apparatus 100 acquires projection data (X-ray projection data) of a subject 200 (workpiece) from 360° directions centering on the subject 200, and constructs a tomographic image 52 (see FIG. 7) based on the acquired projection data. It should be noted that, in the present embodiment, a lithium ion battery will be described as an example of the subject 200, but the subject 200 is not limited to this.

As shown in FIG. 1, the X-ray CT apparatus 100 includes an imaging unit 10. The imaging unit 10 of the X-ray CT apparatus 100 includes an X-ray irradiator 11, an X-ray detector 12, and a rotation stage 13 on which the subject 200 is placed.

The X-ray irradiator 11 emits X-rays. The X-ray irradiator 11 includes an X-ray source (not shown). The X-ray irradiator 11 irradiates the subject 200 with the X-rays. The X-ray detector 12 detects the X-rays emitted from the X-ray irradiator 11 and transmitted through the subject 200. The X-ray irradiator 11 and the X-ray detector 12 are disposed to face each other. The X-ray irradiator 11 and the X-ray detector 12 are disposed to face each other in an X direction (see FIG. 1).

The rotation stage 13 is disposed between the X-ray irradiator 11 and the X-ray detector 12 in the X direction. Moreover, the rotation stage 13 is rotated between X-ray irradiator 11 and X-ray detector 12 around an R axis (see FIG. 1) extending in a Z direction orthogonal to the X direction and a Y direction to rotate the placed subject 200. It should be noted that the rotation stage 13 is configured to be moved in the X direction.

The X-ray CT apparatus 100 acquires the projection data of the subject 200 while rotating the subject 200 by 360° using the rotation stage 13. Moreover, the X-ray CT apparatus 100 constructs the tomographic image 52 (see FIG. 7) based on the acquired projection data. As a result, an internal structure of the subject 200 is perceived three-dimensionally.

Figure 2:
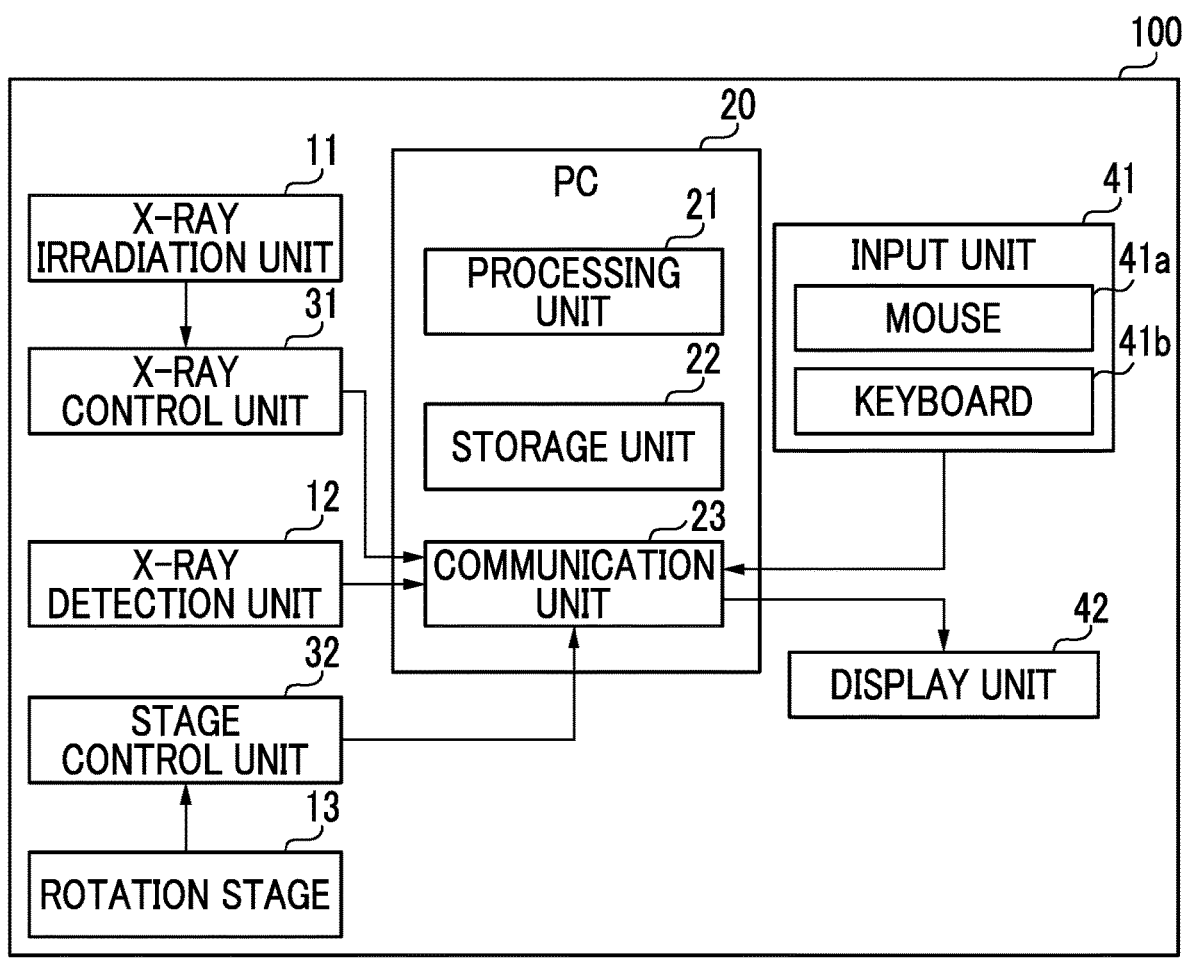
FIG. 2 is a block diagram showing the overall configuration of the X-ray CT apparatus according to the embodiment of the present invention.

In addition, as shown in FIGS. 1 and 2, the X-ray CT apparatus 100 includes a personal computer (PC) 20, an X-ray control unit 31 that controls the irradiation with the X-rays by the X-ray irradiator 11, a stage control unit 32 that controls the rotation of the rotation stage 13. The X-ray control unit 31 controls the irradiation with the X-rays by the X-ray irradiator 11 based on the control by the PC 20. In addition, the stage control unit 32 controls rotation of the rotation stage 13 based on control by the PC 20.

In addition, as shown in FIG. 2, the PC 20 also includes a processor 21, a storage unit 22, and a communication unit 23.

The processor 21 includes a central processor (CPU), a read only memory (ROM), a random access memory (RAM), and the like. The processor 21 is a processor, for example. The processor 21 controls the operations of the X-ray irradiator 11 and the rotation stage 13 through the X-ray control unit 31 and the stage control unit 32, respectively.

In the storage unit 22, software for controlling the X-ray CT apparatus 100, software for executing processing (tomographic image construction processing) of constructing the tomographic image 52 (see FIG. 7) based on the projection data, software for executing processing (region-of-interest reconstruction processing) of reconstructing the tomographic image 52 based on Hilbert transformation described below are stored (loaded). The storage unit 22 includes a non-volatile memory, a hard disk drive (HDD), or a solid state drive (SSD).

The processor 21 controls the entire X-ray CT apparatus 100 by executing programs of software stored in the storage unit 22. In addition, the tomographic image construction processing, the region-of-interest reconstruction processing, processing related to various graphical user interfaces (GUIs), and the like are also performed by the processor 21 executing the corresponding programs.

The communication unit 23 is a communication interface. The PC 20 is communicably connected to each of the X-ray detector 12, the X-ray control unit 31, and the stage control unit 32 by the communication unit 23.

In addition, as shown in FIGS. 1 and 2, the X-ray CT apparatus 100 also includes an input device 41 and a display device 42. The input device 41 and the display device 42 are communicably connected to the communication unit 23 of the PC 20.

The input device 41 is an input device for performing input to the GUI. The input device 41 includes a mouse 41a and a keyboard 41b. In addition, the input device 41 may include a trackball, a touch panel, or the like. The input device 41 receives an input operation by the user and outputs a signal based on the received input operation to the PC 20.

The display device 42 includes a liquid crystal display or an organic EL display, for example. An image output from the PC 20 is displayed on the display device 42. It should be noted that the display device 42 may be a touch panel display provided with a touch panel.

The processor 21 performs the tomographic image construction processing of constructing the tomographic image 52 of the subject 200 based on the projection data acquired by irradiating the subject 200 with the X-rays from a plurality of angles while rotating the subject 200.

Figure 4:
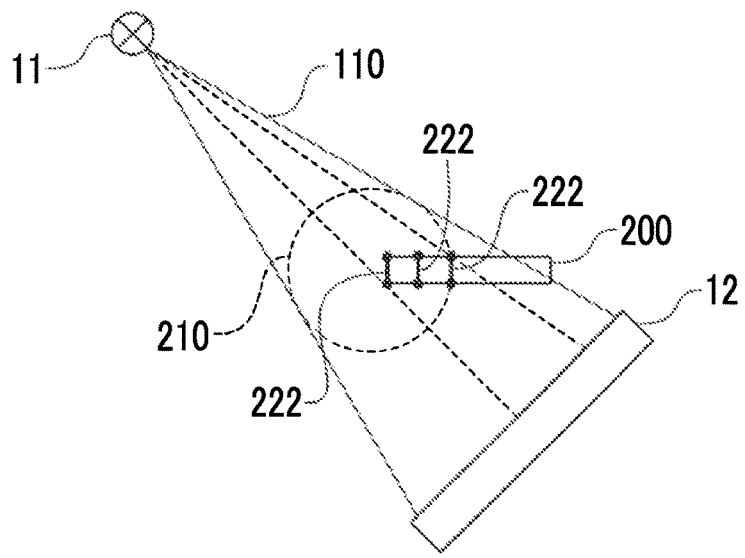
FIG. 4 is a second diagram for describing the region-of-interest reconstruction processing of the X-ray CT apparatus according to the embodiment of the present invention.

In addition, the processor 21 executes the Hilbert transformation to perform the region-of-interest reconstruction processing of reconstructing the tomographic image 52 of the subject 200 in a region of interest (ROI) 210 (see FIG. 4).

In the region-of-interest reconstruction processing, the processor 21 performs processing of displaying, on the display device 42, a GUI for setting or adjusting the region of interest 210 in the rotation axis direction (Z direction) of the subject 200 for which the tomographic image 52 is reconstructed. In addition, in the region-of-interest reconstruction processing, the processor 21 performs processing of displaying, on the display device 42, a GUI for setting or adjusting a Hilbert transformation region 220 (see FIG. 5) on which processing by the Hilbert transformation is performed. It should be noted that details of the GUI for setting or adjusting the Hilbert transformation region 220 and the GUI for setting or adjusting the region of interest 210 in the rotation axis direction of the subject 200 will be described below.

Region-of-Interest Reconstruction Processing

Here, the region-of-interest reconstruction processing executed by the X-ray CT apparatus 100 (processor 21) according to the present embodiment will be described with reference to FIGS. 3 to 6. In the region-of-interest reconstruction processing, the Hilbert transformation is executed to reconstruct the tomographic image 52 of the subject 200 in the region of interest 210. It should be noted that the region of interest 210 is a columnar region extending in the Z direction.

Figure 3:
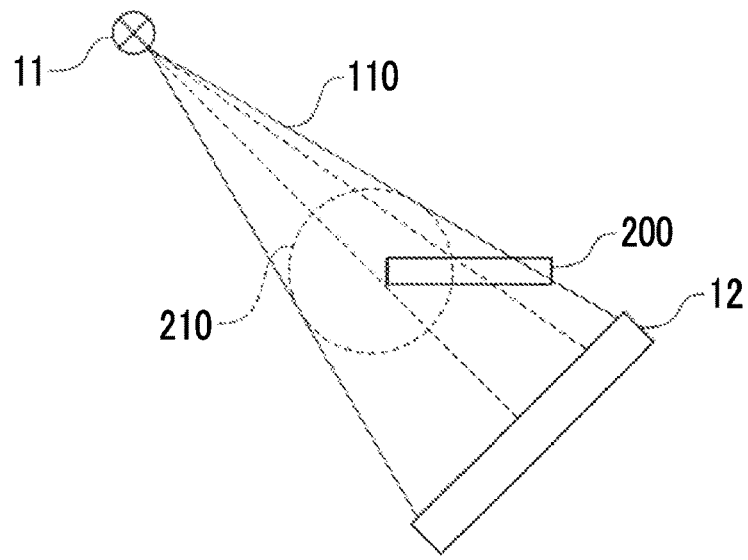
FIG. 3 is a first diagram for describing region-of-interest reconstruction processing of the X-ray CT apparatus according to the embodiment of the present invention.

In a case in which the subject 200 is brought closer to the X-ray irradiator 11 and a magnification ratio is increased to image a part of the subject 200, as shown in FIG. 3, the projection data is acquired while rotating the subject 200 in a state in which a part of the subject 200 is included in the X-ray irradiation region 110 and the other part protrudes from the X-ray irradiation region 110. In such a case, in the projection data acquired by the X-ray detector 12, projection data transmitted through a region other than the subject 200, such as air, in the region of interest 210 and projection data transmitted through the protruding part (truncation part) of the subject 200 protruding outside the region of interest 210 are unnecessary data in the reconstruction of the tomographic image 52. In particular, the projection data of the protruding part of the subject 200 that protrudes outside the region of interest 210 causes information contradiction in a case of constructing the tomographic image 52, resulting in the generation of the artifact (noise).

The Hilbert transformation performed by the processor 21 is performed by using the following expressions (1) to (3). The artifact (noise) caused by the protruding part of the subject 200 is reduced by the Hilbert transformation executed by using the following expressions (1) to (3).

$$f(t) = \frac{1}{W(t)} \left( C_{af} + \frac{1}{\pi} p.v. \int_a^f ds \frac{1}{s-t} g(s)W(s) \right) \quad (a < t < f) \quad (1)$$

$$W(t) = \sqrt{(f-t)(t-a)} \quad (2)$$

$$C_{af} = \frac{1}{\pi} \int_a^f dt f(t) \quad (3)$$

Figure 5:
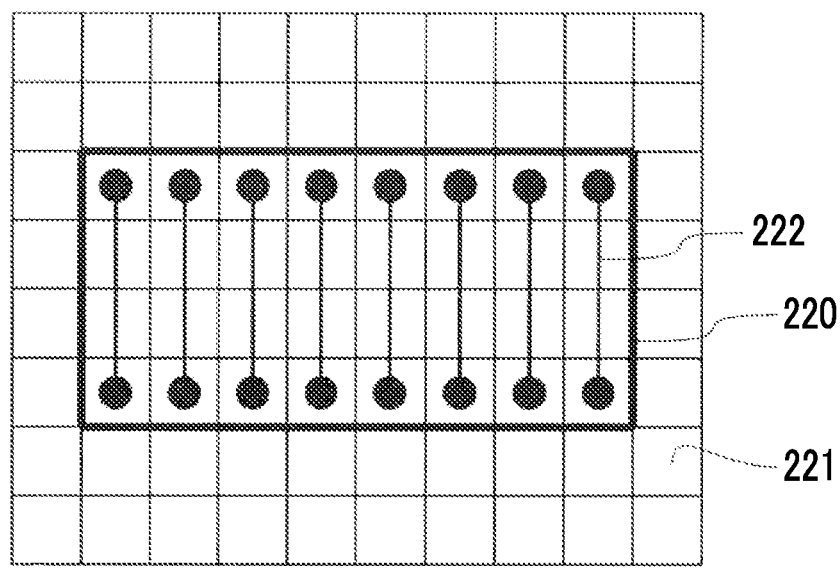
FIG. 5 is a diagram for describing a code and a Hilbert transformation region.
Figure 6:
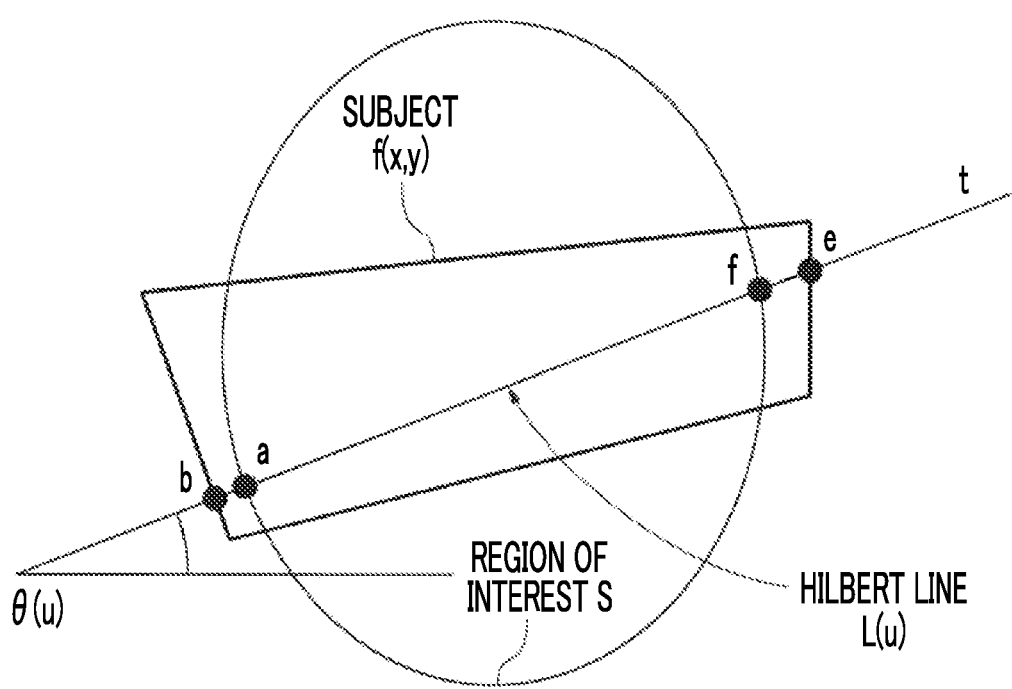
FIG. 6 is a diagram showing a relationship between a subject, a region of interest, and a Hilbert line.

Here, in order to set a region for which the data is transformed by the Hilbert transformation, the processor 21 needs to set a code 222 (see FIGS. 4 and 5). The code 222 corresponds to a region in the region of interest 210 on which the Hilbert transformation is performed. It should be noted that, although FIG. 4 shows the codes 222 only at one end part, a center part, and the other end part of the subject 200 for the sake of simplification, in practice, a plurality of codes 222 are set from one end to the other end of the subject 200 in the region of interest 210. In the reconstruction of the tomographic image 52, in order to perform the Hilbert transformation on the data of the tomographic image 52 based on the projection data, the processor 21 sets a position of the code (n line) 222, which is a set of voxels 221 (see FIG. 5) of the data of the tomographic image 52, a width of the code 222, and an angle of the code 222. It should be noted that the voxel 221 is a value in regular grid units in a three-dimensional space. In addition, the code 222 corresponds to a line segment (line segment af) connecting a point a and a point f on a Hilbert line shown in FIG. 6. In the present embodiment, the processor 21 sets the position of the code 222, the width of the code 222, and the angle of the code 222 based on the Hilbert transformation region 220 (see FIG. 5), which is a set of the codes 222. That is, the Hilbert transformation region 220 is a set of the line segments (line segments af) connecting the point a and the point f on the Hilbert line. It should be noted that, although FIG. 5 shows an example in which all the codes 222 have the same width, the codes 222 may have different widths. That is, the Hilbert transformation region 220, which is a set of the codes 222, is not limited to a rectangular shape as shown in FIG. 5.

GUI

The image including various GUIs are displayed on the display device 42 under the control of the processor 21. Specifically, the display device 42 displays a window 50 (see FIG. 7). Moreover, as shown in FIGS. 7 to 13, the window 50 displayed on the display device 42 displays the X-ray projection image 51 based on the projection data, the tomographic image 52 constructed by the processor 21, and the various GUIs. Specifically, the display device 42 displays a check box 71 (see FIG. 7), a region-of-interest GUI 72 (see FIG. 8), and a transformation region GUI 73 (see FIG. 8) are displayed in the window 50 together with the X-ray projection image 51 and the tomographic image 52. In addition, the display device 42 also displays a tomographic image position GUI 81 (see FIG. 7) and a region-of-interest GUI 82 (see FIG. 8) in the window 50. It should be noted that the check box 71 and the region-of-interest GUI 82 are examples of a "GUI, which is a graphical user interface" in the scope of claims. In addition, the check box 71 is an example of a "region-of-interest automatic setting GUI" in the scope of claims. It should be noted that the region-of-interest GUI 82 is an example of a "rotation axis direction region-of-interest GUI" in the scope of claims.

The processor 21 performs processing of setting or adjusting the Hilbert transformation region 220 according to the input to the GUI from the input device 41. Specifically, the processor 21 receives the input from the user to the GUI through the mouse 41*a* and the keyboard 41*b*, and sets or adjusts the Hilbert transformation region 220 according to the received input.

The check box 71 is a GUI for setting the Hilbert transformation region 220. In addition, the check box 71 is a GUI for setting the region of interest 210 in the rotation axis direction (Z direction) of the subject 200. In addition, the check box 71 is a GUI used in a case of switching to a mode (see FIGS. 8 to 13) for setting the region of interest 210 and the Hilbert transformation region 220 for which the region-of-interest reconstruction processing is executed. The processor 21 performs processing of switching to a mode for setting the region of interest 210 and the Hilbert transformation region 220 for which the region-of-interest reconstruction processing is executed, by the user operating a cursor 60 using the mouse 41*a* to perform an operation of checking the check box 71. It should be noted that, in a case in which the cursor 60 is superimposed on the GUIs (region-of-interest GUI 72, transformation region GUI 73, tomographic image position GUI 81, and region-of-interest GUI 82) displayed in a superimposed manner on the X-ray projection image 51 and the tomographic image 52, a cursor shape is changed from an arrow shape (see FIG. 7) to a hand-like shape (see FIG. 8).

Figure 8:
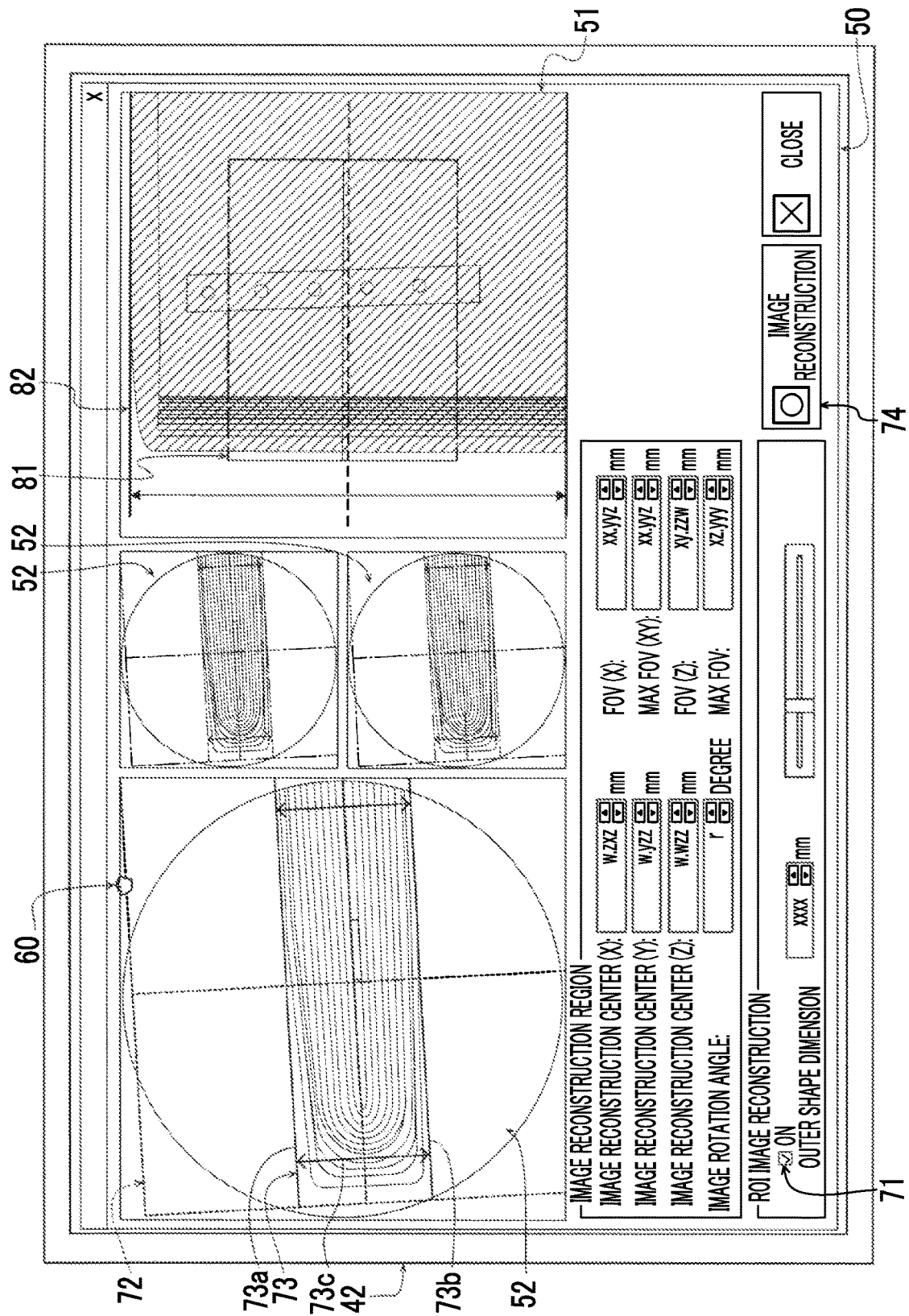
FIG. 8 is a diagram showing a region-of-interest GUI and a transformation region GUI.

Moreover, the check box 71 is a GUI for the processor 21 to automatically set the Hilbert transformation region 220. In the present embodiment, as shown in FIG. 8, in a case in which the check box 71 is checked to switch to the mode for setting the region of interest 210 and the Hilbert transformation region 220, the transformation region GUI 73 corresponding to the Hilbert transformation region 220, which has been automatically set by the processor 21, is displayed on the display device 42. That is, the processor 21 performs processing of displaying, on the display device 42, the transformation region GUI 73 indicating the Hilbert transformation region 220 which has been automatically set by the processor 21. It should be noted that details of the automatic setting of the Hilbert transformation region 220 by the processor 21 will be described below.

In addition, the check box 71 is a GUI for the processor 21 to automatically set the region of interest 210 in the rotation axis direction (Z direction) of the subject 200. In the present embodiment, as shown in FIG. 8, in a case in which the check box 71 is checked to switch to the mode for setting the region of interest 210 and the Hilbert transformation region 220, the region-of-interest GUI 82 corresponding to the region of interest 210 in the rotation axis direction (Z direction) of the subject 200, which has been automatically set by the processor 21, is displayed on the display device 42. That is, the processor 21 performs processing of displaying, on the display device 42, the region-of-interest GUI 82 corresponding to the region of interest 210 in the rotation axis direction (Z direction) of the subject 200 which has been automatically set by the processor 21. It should be noted that the details of the automatic setting of the region of interest 210 in the rotation axis direction (Z direction) of the subject 200 by the processor 21 will be described below.

The processor 21 performs processing of displaying, on the display device 42, the tomographic image position GUI 81 in a superimposed manner on the X-ray projection image 51. The tomographic image position GUI 81 indicates the position of the tomographic image 52 displayed in the window 50 in the rotation axis direction (Z direction) of the subject 200. Specifically, the tomographic image 52 corresponding to the position of one end of the tomographic image position GUI 81 is displayed at the upper center in the window 50 (above the center in FIG. 7). In addition, the tomographic image 52 corresponding to the position of the other end of the tomographic image position GUI 81 is displayed at the lower center in the window 50 (below the center in FIG. 7). Moreover, the tomographic image 52 corresponding to the central position of the tomographic image position GUI 81 is displayed on the left side in the window 50 (left in FIG. 7).

The region-of-interest GUI 72 (see FIG. 8) indicates the region of interest 210 in a direction along an XY plane orthogonal to the rotation axis direction (Z direction). In addition, the region-of-interest GUI 72 is a GUI for adjusting the region of interest 210 in the direction along the XY plane orthogonal to the rotation axis direction (Z direction). It should be noted that the region-of-interest GUI 72 is displayed in a frame shape.

In addition, the transformation region GUI 73 is a GUI indicating the Hilbert transformation region 220. Moreover, the transformation region GUI 73 is a GUI for adjusting the Hilbert transformation region 220. The transformation region GUI 73 indicates the Hilbert transformation region 220 in the direction along the XY plane orthogonal to the rotation axis direction (Z direction). That is, the transformation region GUI 73 indicates the Hilbert transformation region 220 in the cross-sectional (XY plane) direction of the subject 200. In addition, the transformation region GUI 73 includes a bar 73*a* indicating one end in a width direction of the Hilbert transformation region 220, a bar 73*b* indicating the other end in the width direction of the Hilbert transformation region 220, and an arrow 73*c* indicating the direction of the code 222 (see FIG. 5) in the Hilbert transformation region 220. That is, an inclination of the arrow 73*c* indicates the angle of the code 222 in the Hilbert transformation region 220.

As shown in FIG. 8, the processor 21 performs the processing of displaying, on the display device 42, the region-of-interest GUI 72 and the transformation region GUI 73 in a superimposed manner on the tomographic image 52. The region-of-interest GUI 72 and the transformation region GUI 73 are displayed in colors with relatively high visibility in a case of being superimposed on the black and white tomographic image 52. For example, the region-of-interest GUI 72 is displayed by a green frame, and the bars 73*a* and 73*b*, and the arrow 73*c* of the transformation region GUI 73 are displayed by red lines.

Moreover, in a case in which the region of the region-of-interest GUI 72 superimposed on the tomographic image 52 is changed, the processor 21 performs the processing of adjusting the Hilbert transformation region 220 such that the transformation region GUI 73 indicating the Hilbert transformation region 220 for the tomographic image 52 is included inside the region-of-interest GUI 72.

Figure 9:
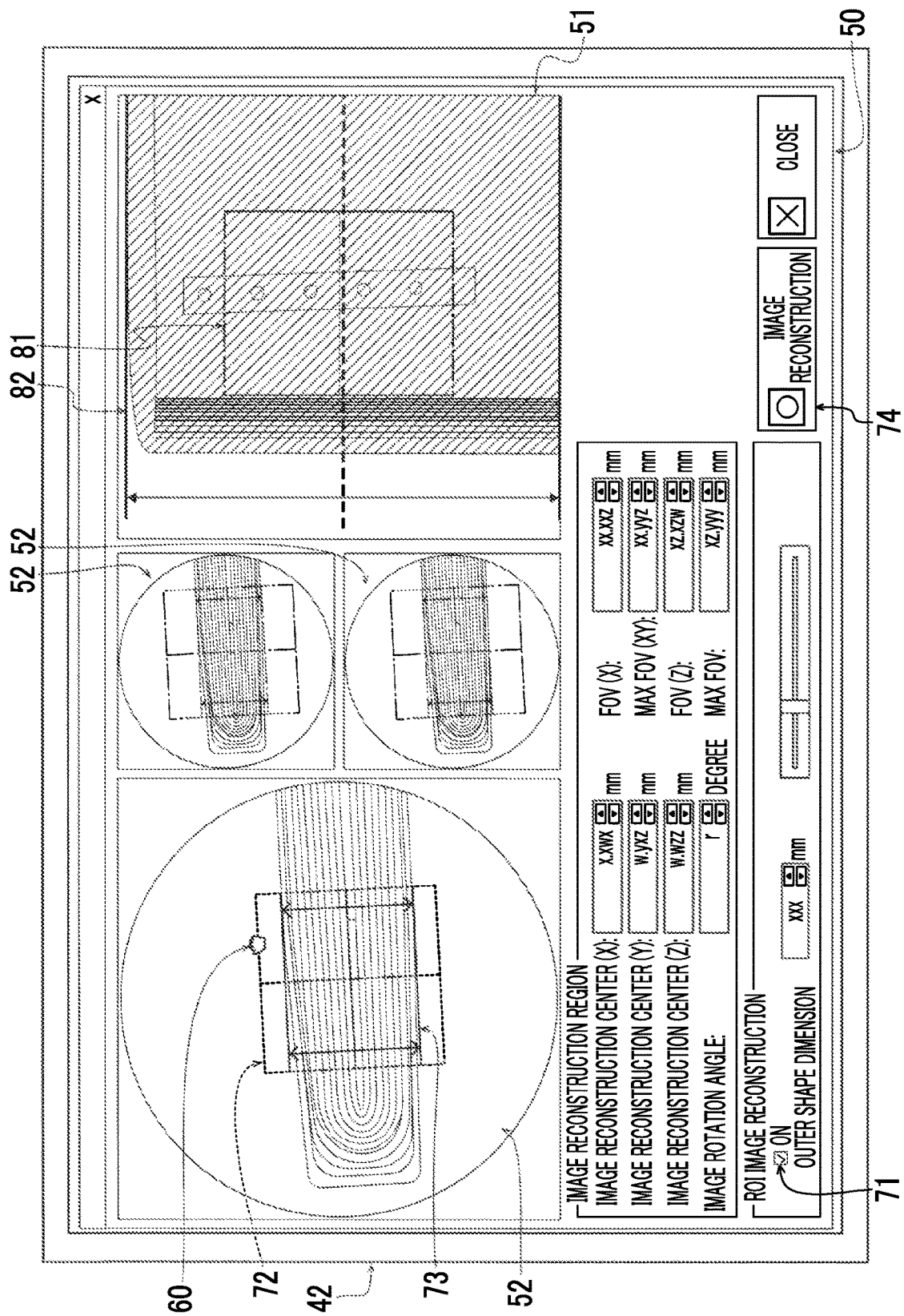
FIG. 9 is a diagram showing the adjustment of the region of interest in a cross-sectional direction using the region-of-interest GUI.

Specifically, as shown in FIG. 8, the processor 21 performs processing of adjusting the region of interest 210 in the cross-sectional (XY plane) direction of the subject 200 by the user using the mouse 41*a* to mouse-drag the frame of the region-of-interest GUI 72 with the cursor 60 to change a size of the frame of the region-of-interest GUI 72. In the present embodiment, as shown in FIG. 9, in the Hilbert transformation region 220 before the size of the region-of-interest GUI 72 is changed, a part that is not included in the region of interest 210 as the size of the region-of-interest GUI 72 is changed is excluded from the Hilbert transformation region 220, and the Hilbert transformation region 220 is changed. Moreover, according to the change of the Hilbert transformation region 220, the display of the transformation region GUI 73 is also changed by the processor 21 to be included inside the region-of-interest GUI 72.

The processor 21 performs processing of adjusting a position of the Hilbert transformation region 220, a width of the Hilbert transformation region 220, and an angle of the Hilbert transformation region 220 for the tomographic image 52, according to the input to the transformation region GUI 73 by the input device 41.

Figure 10:
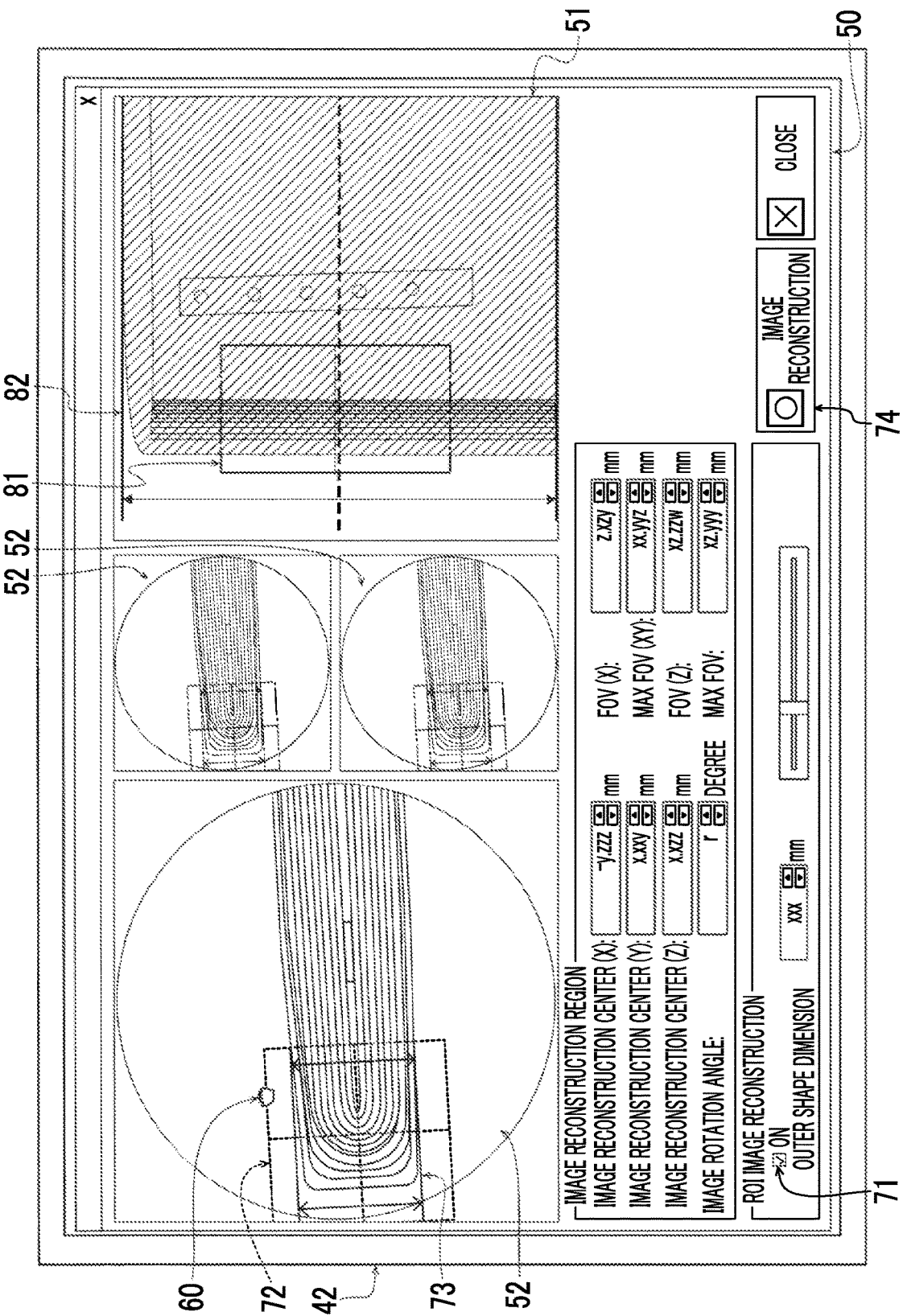
FIG. 10 is a first diagram showing the adjustment of the Hilbert transformation region using the transformation region GUI.

Specifically, as shown in FIG. 10, the processor 21 performs the processing of adjusting the position of the Hilbert transformation region 220 by the user operating the cursor 60 with the mouse 41*a* to mouse-drag and move the transformation region GUI 73 the Hilbert transformation region 220.

Figure 11:
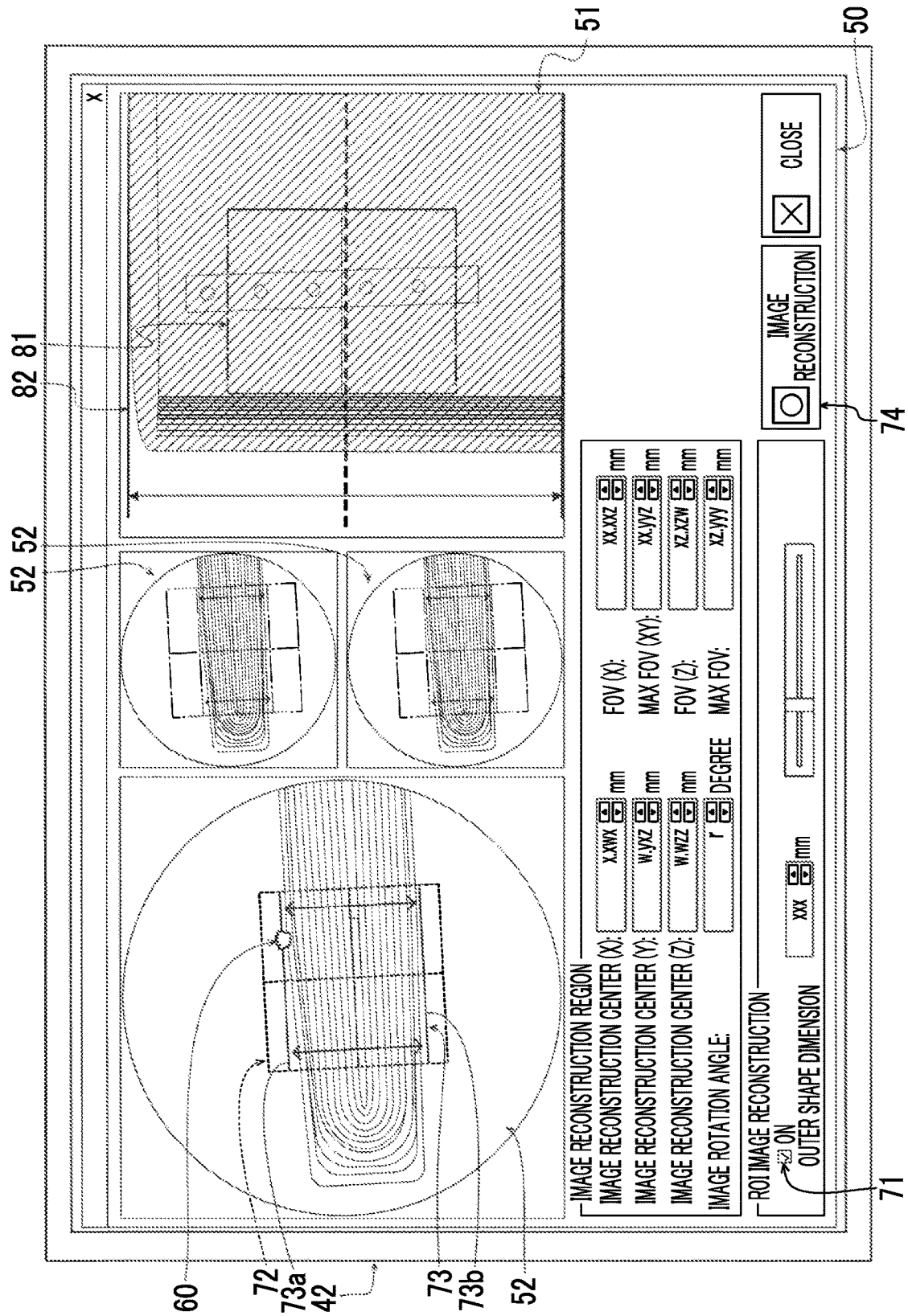
FIG. 11 is a second diagram showing the adjustment of the Hilbert transformation region using the transformation region GUI.

In addition, as shown in FIG. 11, the processor 21 performs the processing of adjusting the width of the Hilbert transformation region 220 by the user operates the cursor 60 with the mouse 41*a* to mouse-drag and slide the bar 73*a* or 73*b* indicating one end of the Hilbert transformation region 220 in the width direction.

Figure 12:
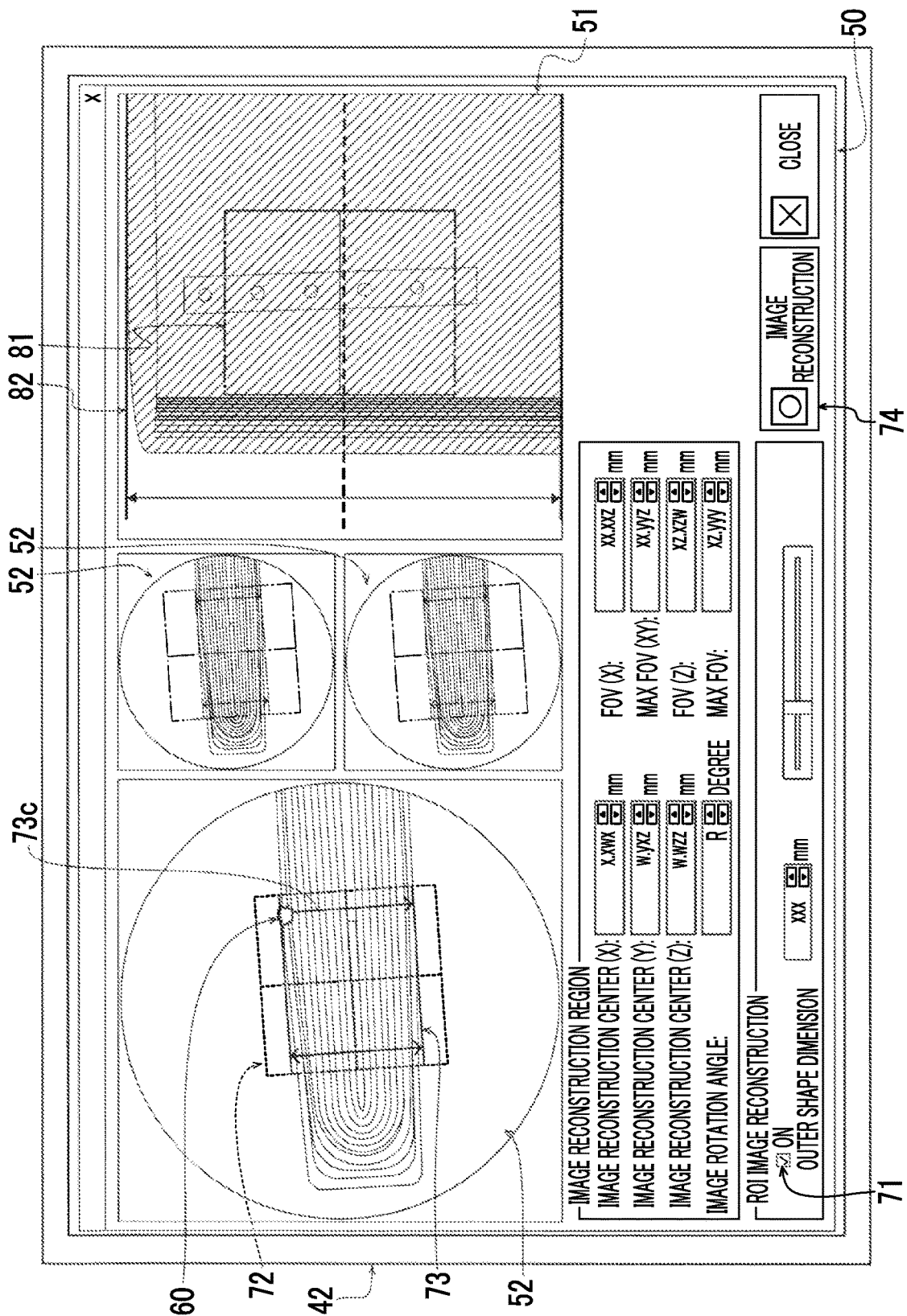
FIG. 12 is a third diagram showing the adjustment of the Hilbert transformation region using the transformation region GUI.

In addition, as shown in FIG. 12, the processor 21 performs the processing of adjusting the angle (angle of the code 222) of the Hilbert transformation region 220 for the tomographic image 52 by the user operating the cursor 60 with the mouse 41*a* to mouse-drag a region in which the angle of the code 222 is changed, such as the arrow 73*c* indicating the angle of the code 222 in the Hilbert transformation region 220, to perform the operation of rotating the transformation region GUI 73 around the axis orthogonal to the screen of the display device 42.

In addition, the processor 21 can also perform processing of changing the Hilbert transformation region 220 by the user using the mouse 41*a* and the keyboard 41*b* to directly input each value (parameter) of "image reconstruction center (X)", "image reconstruction center (Y)", "image reconstruction center (Z)", and "image rotation angle" displayed on the window 50.

In addition, in a case in which the Hilbert transformation region 220 is adjusted (set) by using the transformation region GUI 73, each value (parameter) of "image reconstruction center (X)", "image reconstruction center (Y)", "image reconstruction center (Z)", and "image rotation angle" displayed on the window 50 is changed by the processor 21 in conjunction with the adjusted (set) value.

GUI for Setting Region of Interest in Z Direction

In addition, as shown in FIGS. 8 to 13, the processor 21 performs processing of displaying the region-of-interest GUI 82 in a superimposed manner on the X-ray projection image 51 on the display device 42. The region-of-interest GUI 82 indicates the region of interest 210 in the rotation axis direction of the subject 200. In addition, the region-of-interest GUI 82 is a GUI for adjusting the region of interest 210 in the rotation axis direction (Z direction) of the subject 200. In addition, the region-of-interest GUI 82 is displayed in colors with relatively high visibility in a case of being superimposed on the black and white X-ray projection image 51. For example, the region-of-interest GUI 82 is displayed by a red line.

The processor 21 performs processing of setting or adjusting the region of interest 210 in the rotation axis direction (Z direction) of the subject 200 according to the input to the region-of-interest GUI 82 by the input device 41. The processor 21 performs processing of adjusting at least the position of the region of interest 210 in the rotation axis direction of the subject 200 according to the input to the region-of-interest GUI 82 by the input device 41.

Figure 13:
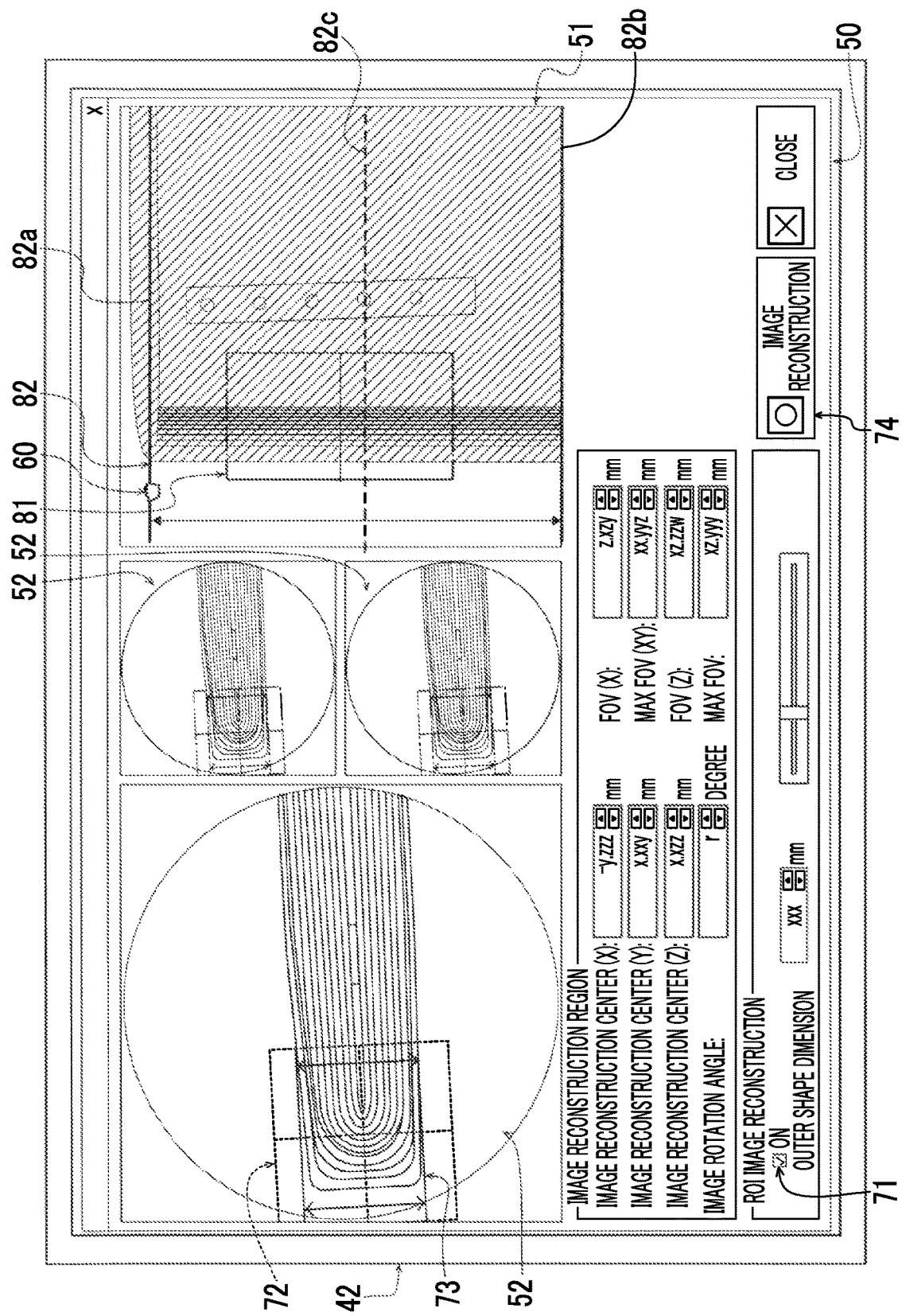
FIG. 13 is a diagram showing the adjustment of the region of interest in a rotation axis direction using the region-of-interest GUI.

In the present embodiment, as shown in FIG. 13, the region-of-interest GUI 82 includes a bar 82*a* indicating one end of the region of interest 210 in the Z direction, a bar 82*b* indicating the other end of the region of interest 210 in the Z direction, and a bar 82*c* indicating the central position of the region of interest 210 in the Z direction.

As shown in FIG. 13, the processor 21 performs processing of adjusting the position of the end part of the region of interest 210 in the rotation axis direction (Z direction) and the width of the region of interest 210 by the user operating the cursor 60 with the mouse 41*a* to mouse-drag and slide the bar 82*a* or 82*b*.

In addition, the position of the entire region of interest 210 in the rotation axis direction (Z direction) indicated by the region-of-interest GUI 82 can be adjusted based on the operation by the user. For example, the processor 21 performs processing of adjusting the entire position of the region of interest 210 in the rotation axis direction (Z direction) indicated by the region-of-interest GUI 82 by the user operating the cursor 60 with the mouse 41*a* to mouse-drag and slide the bar 82*c*.

In addition, the processor 21 also can perform processing of changing the region of interest 210 in the rotation axis direction (Z direction) of the subject 200 by the user directly inputting a value (parameter) of "FOV (Z)" displayed on the window 50 through the mouse 41*a* and the keyboard 41*b*.

In addition, in a case in which the region of interest 210 in the rotation axis direction (Z direction) of the subject 200 is adjusted (set) by using the region-of-interest GUI 82, the value of "FOV (Z)" displayed on the window 50 is changed by the processor 21 in conjunction with the adjusted (set) value.

Moreover, in a case in which input to an image reconstruction start button 74 is performed by the input device 41 (mouse 41*a* and keyboard 41*b*), the processor 21 executes the region-of-interest reconstruction processing of reconstructing the tomographic image 52 according to the region of interest 210 which has been set or adjusted by using various GUIs and the Hilbert transformation region 220.

Configuration for Automatic Setting of Hilbert Transformation Region

In the present embodiment, the processor 21 performs processing of automatically setting the Hilbert transformation region 220 corresponding to a shape of the subject 200 based on a detection result of the X-ray detector 12.

The processor 21 performs the processing of automatically setting the Hilbert transformation region 220 based on the input to the check box 71 by the input device 41. Specifically, in a case in which the check box 71 is checked, the processing of automatically setting the Hilbert transformation region 220 is executed by the processor 21 simultaneously with the processing of switching to the mode for setting the region of interest 210 for which the region-of-interest reconstruction processing is executed and the Hilbert transformation region 220.

Configuration for Automatic Setting of Region of Interest

In the present embodiment, the processor 21 performs processing of automatically setting the region of interest 210 in the rotation axis direction of the subject 200 corresponding to the size of the subject 200 in the rotation axis direction based on the detection result of the X-ray detector 12.

The processor 21 performs the processing of automatically setting the region of interest 210 in the rotation axis direction (Z direction) of the subject 200 based on the input to the check box 71. Specifically, in a case in which the check box 71 is checked, the processing of automatically setting the region of interest 210 in the rotation axis direction of the subject 200 is executed by the processor 21 simultaneously with the processing of switching to the mode for setting the region of interest 210 for which the region-of-interest reconstruction processing is executed and the Hilbert transformation region 220. That is, in a case in which the check box 71 is checked, the processing of automatically setting the Hilbert transformation region 220 and the processing of automatically setting the region of interest 210 in the rotation axis direction of the subject 200 are executed by the processor 21 simultaneously with the processing of switching to the mode for setting the region of interest 210 and the Hilbert transformation region 220.

Figure 14:
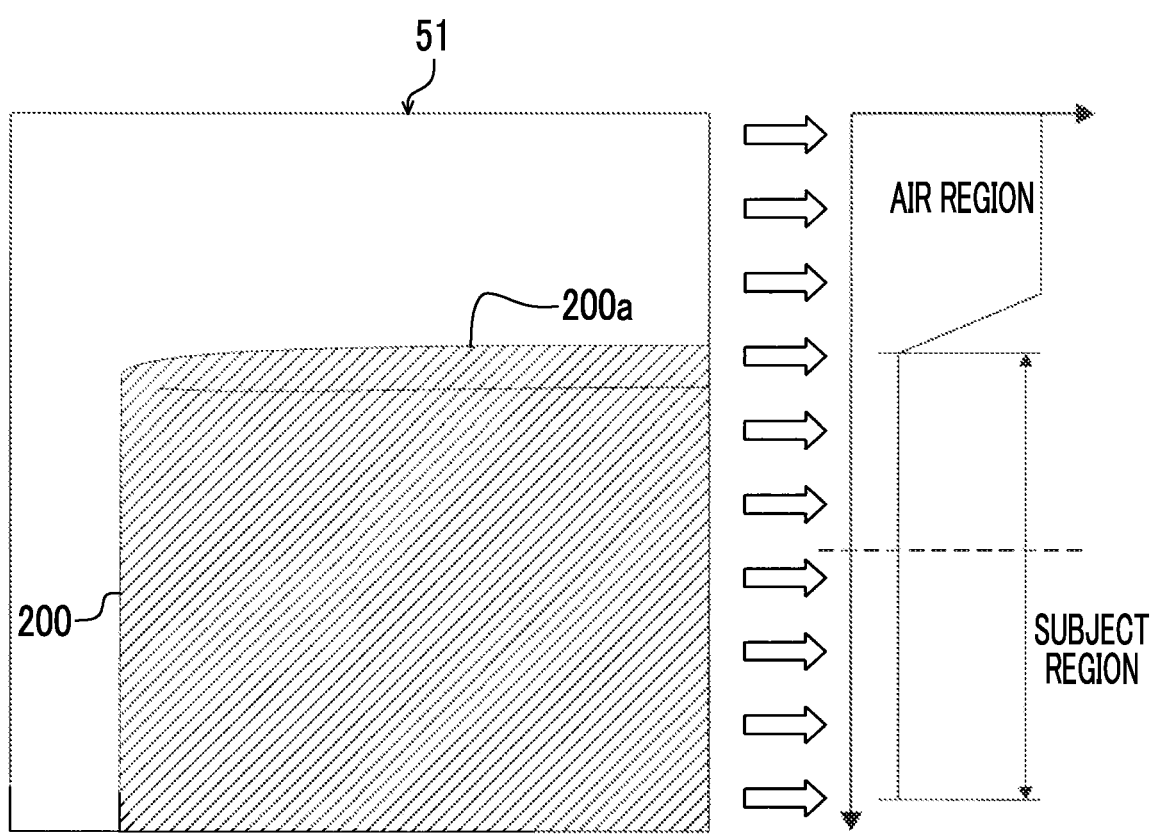
FIG. 14 is a diagram for describing an example of automatic setting processing of the region of interest based on an X-ray projection image.

In the present embodiment, as shown in FIG. 14, the processor 21 performs processing of acquiring a position of an end part 200a in the rotation axis direction of the subject 200 based on a change in a brightness value of the X-ray projection image 51, as the detection result of the X-ray detector 12, in the rotation axis direction of the subject 200. Moreover, the processor 21 performs processing of automatically setting the position of the region of interest 210 in the rotation axis direction of the subject 200 based on the acquired position of the end part 200a in the rotation axis direction of the subject 200.

As shown in FIG. 14, the processor 21 creates a profile of the change in the brightness value of the X-ray projection image 51 (projection data) integrated in a horizontal direction orthogonal to the rotation axis direction of the subject 200, in the rotation axis direction (Z direction). The processor 21 detects a region having a certain brightness value in the created profile. Moreover, the processor 21 detects each of a region (subject region) of the subject 200 and a region (air region) other than the subject 200 from the region having a certain brightness value in the created profile based on a size relationship of the brightness value between the region (subject region) of the subject 200 and the region (air region) other than the subject 200. Further, the processor 21 detects a boundary between the subject region and the air region, and acquires the position of the end part of the subject region as the position of the end part 200a of the subject 200 in the rotation axis direction (Z direction).

It should be noted that, in the present embodiment, as shown in FIG. 14, the processor 21 detects the position at which the change in the brightness value ends between the subject region and the air region as the boundary between the subject region and the air region. It should be noted that the processor 21 may detect the position at which the change in the brightness value starts between the subject region and the air region as the boundary between the subject region and the air region. In addition, the processor 21 may detect an intermediate position between the position at which the change in the brightness value starts between the subject region and the air region, and the position at which the change in the brightness value ends between the subject region and the air region, as the boundary between the subject region and the air region.

Moreover, the processor 21 performs the processing of automatically setting the position of the region of interest 210 in the rotation axis direction (Z direction) of the subject 200 from the acquired position of the end part 200a in the rotation axis direction of the subject 200.

In addition, the processor 21 performs the processing of displaying, on the display device 42, the region-of-interest GUI 82 indicating the region of interest 210 in the rotation axis direction of the subject 200 which has been automatically set by the processor 21 based on the change in the brightness value of the X-ray projection image 51 in the rotation axis direction of the subject 200. As described above, in a case in which the operation of checking the check box 71 is performed, the region-of-interest GUI 82 (see FIG. 8) indicating the region of interest 210 in the rotation axis direction of the subject 200, which has been automatically set by the processor 21 based on the change in the brightness value of the X-ray projection image 51 in the rotation axis direction of the subject 200, is displayed in the window 50 of the display device 42.

Region-of-Interest Reconstruction Processing

Figure 15:
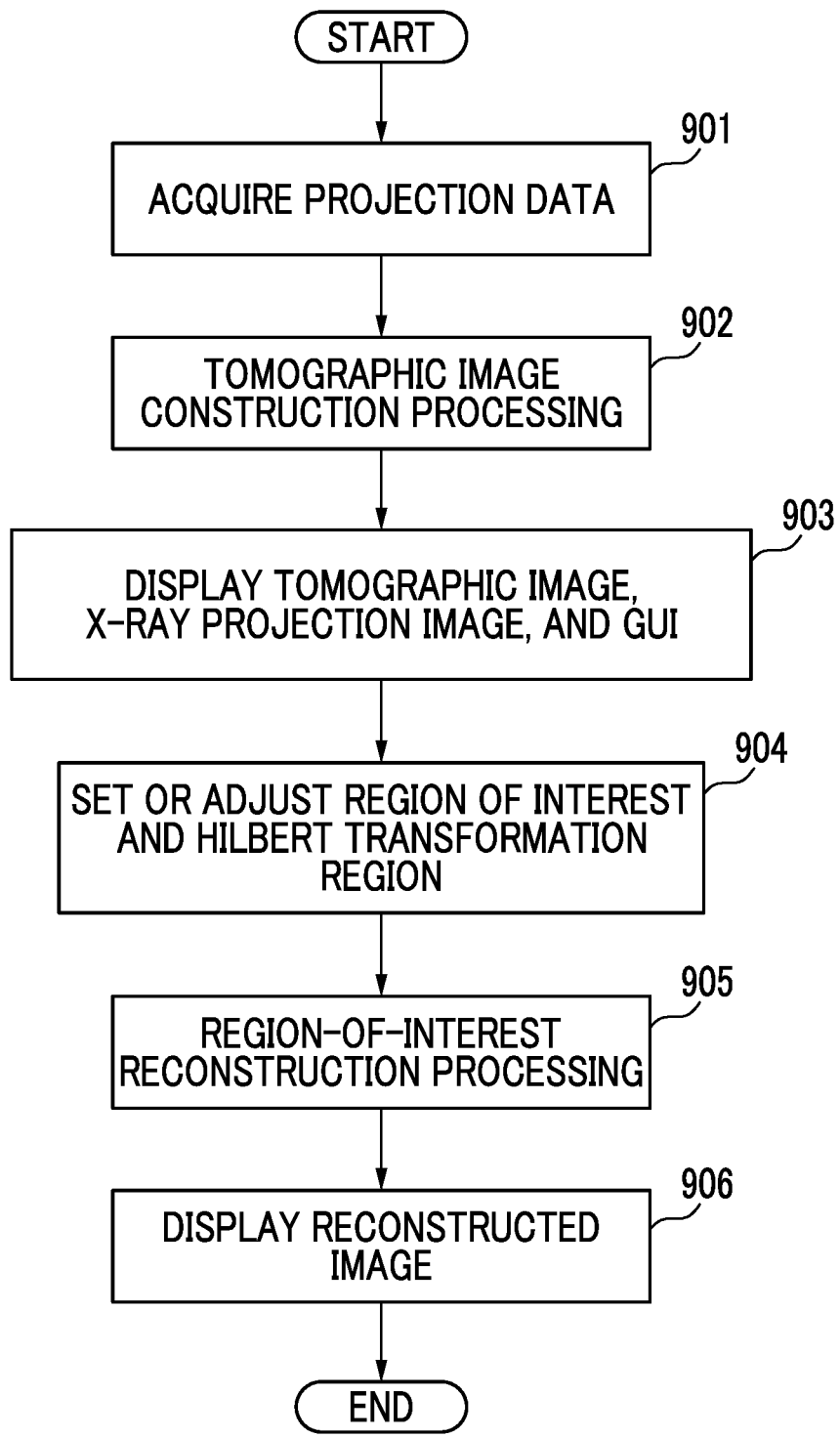
FIG. 15 is a flowchart showing an example of the region-of-interest reconstruction processing by the X-ray CT apparatus according to the embodiment of the present invention.

Next, a processing flow of the region-of-interest reconstruction processing by the X-ray CT apparatus 100 according to the present embodiment will be described with reference to FIG. 15.

First, in step 901, the projection data is acquired. In step 901, the projection data acquired by emitting the X-rays from a plurality of angles while rotating the subject 200 is acquired. After step 901 is completed, the processing step proceeds to step 902.

In step 902, the tomographic image construction processing is performed. In step 902, the processor 21 performs the tomographic image construction processing of constructing the tomographic image 52 of the subject 200 based on the projection data acquired by irradiating the subject 200 with the X-rays from a plurality of angles. It should be noted that step 902 is an example of a "tomographic image construction processing step" in the scope of claims. After step 902 is completed, the processing step proceeds to step 903.

In step 903, the X-ray projection image 51, the tomographic image 52, and the GUI are displayed. In step 903, as described above, the GUI for setting or adjusting the region of interest 210 in the rotation axis direction of the subject 200 is displayed together with the X-ray projection image 51 and the tomographic image 52. In step 903, in the region-of-interest reconstruction processing of reconstructing the tomographic image 52 of the subject 200 in the region of interest 210 by executing the Hilbert transformation, the processor 21 displays the GUI (check box 71 or region-of-interest GUI 82) for setting or adjusting the region of interest 210 in the rotation axis direction of the subject 200 for which the tomographic image 52 is reconstructed. It should be noted that step 903 is an example of a "projection image display step" and a "GUI display step" in the scope of claims. After step 903 is completed, the processing step proceeds to step 904.

In step 904, each region of the region of interest 210 and the Hilbert transformation region 220 is set or adjusted. As described above, the user sets or adjusts each region of the region of interest 210 and the Hilbert transformation region 220 by using the GUI. Moreover, after each region of the region of interest 210 and the Hilbert transformation region 220 has been set or adjusted, the processing step proceeds to step 905 by pressing the image reconstruction start button 74.

In step 905, the region-of-interest reconstruction processing is performed. In step 905, the processor 21 performs the region-of-interest reconstruction processing based on the region of interest 210 in the rotation axis direction of the subject 200 which has been set or adjusted by using the GUI in step 904. It should be noted that step 905 is an example of a "region-of-interest reconstruction processing step" in the scope of claims. After step 905 is completed, the processing step proceeds to step 906.

Moreover, in step 906, a reconstructed image obtained by reconstructing the tomographic image 52 is displayed. In step 906, the reconstructed image created by the region-of-interest reconstruction processing of the processor 21 is displayed.

Effects of Present Embodiment

In the present embodiment, the following effects can be obtained.

In the present embodiment, the X-ray projection image 51 based on the projection data is displayed, and the GUI for setting or adjusting the region of interest 210 in the rotation axis direction (Z direction) of the subject 200 is also displayed, so that the user can appropriately set or adjust the region of interest 210 in the rotation axis direction of the subject 200 by using the GUI while visually recognizing the X-ray projection image 51 based on the projection data of the subject 200 and accurately grasping the position of the subject 200 in the rotation axis direction. As a result, it is possible to provide the X-ray CT apparatus 100 and the reconstruction method of the tomographic image 52 which can appropriately and easily set or adjust the region of interest 210 in the rotation axis direction of the subject 200 depending on the subject 200.

In addition, with the X-ray CT apparatus 100 according to the embodiment described above, the following further effects are obtained by the configuration as below.

In addition, in the X-ray CT apparatus 100 according to the present embodiment, the processor 21 performs the processing of displaying, on the display device 42, the region-of-interest GUI 82 (rotation axis direction region-of-interest GUI) in a superimposed manner on the X-ray projection image 51. As a result, the region-of-interest GUI 82 is displayed in a superimposed manner on the X-ray projection image 51, so that the user can appropriately and more easily set or adjust the region of interest 210 such that the region-of-interest GUI 82 indicating the region of interest 210 in the rotation axis direction of the subject 200 is superimposed on the subject 200 in the X-ray projection image 51. As a result, it is possible for the user to more appropriately and easily set or adjust the region of interest 210 in the rotation axis direction of the subject 200 depending on the subject 200.

In addition, the X-ray CT apparatus 100 according to the present embodiment also includes the input device 41 for performing the input to the GUI. Moreover, the processor 21 performs the processing of setting or adjusting the region of interest 210 in the rotation axis direction (Z direction) of the subject 200 according to the input to the GUI from the input device 41. As a result, it is possible for the user to easily set or adjust the region of interest 210 in the rotation axis direction of the subject 200 by performing the input to the GUI with the input device 41. As a result, the region of interest 210 in the rotation axis direction of the subject 200 can be easily set or adjusted in a range of the region desired by the user.

In addition, in the X-ray CT apparatus 100 according to the present embodiment, the processor 21 performs the processing of adjusting at least the position of the region of interest 210 in the rotation axis direction (Z direction) of the subject 200 according to the input to the region-of-interest GUI 82 (rotation axis direction region-of-interest GUI) by the input device 41. As a result, it is possible for the user to adjust the position of the region of interest 210 in the rotation axis direction of the subject 200 by performing the input to the region-of-interest GUI 82. As a result, it is possible for the user to adjust the position of the region of interest 210 in the rotation axis direction of the subject 200 depending on the subject 200 by performing the input to the region-of-interest GUI 82.

In addition, in the X-ray CT apparatus 100 according to the present embodiment, the processor 21 performs the processing of automatically setting the region of interest 210 in the rotation axis direction (Z direction) of the subject 200 based on the input to the check box 71 (region-of-interest automatic setting GUI). As a result, since the region of interest 210 in the rotation axis direction of the subject 200 is automatically set by the processor 21, it is possible to more easily set the region of interest 210 in the rotation axis direction of the subject 200 than a case in which the region of interest 210 in the rotation axis direction of the subject 200 is set (adjusted) only by the manual input by the user.

In addition, in the X-ray CT apparatus 100 according to the present embodiment, the processor 21 performs the processing of automatically setting the region of interest 210 in the rotation axis direction (Z direction) of the subject 200 corresponding to the size of the subject 200 in the rotation axis direction based on the detection result of the X-ray detector 12. As a result, since the region of interest 210 corresponding to the size in the rotation axis direction of the subject 200 is automatically set by the processor 21, it is possible to more easily set the region of interest 210 corresponding to the size in the rotation axis direction of the subject 200 than a case in which the region of interest 210 is set (adjusted) only by the manual input by the user. In addition, the processor 21 performs the processing of displaying, on the display device 42, the region-of-interest GUI 82 (rotation axis direction region-of-interest GUI) indicating the region of interest 210 in the rotation axis direction of the subject 200 which has been automatically set by the processor 21. As a result, it is possible for the user to grasp the region of interest 210 in the rotation axis direction of the subject 200, which has been automatically set by the processor 21 based on the detection result of the X-ray detector 12, by visually recognizing the region-of-interest GUI 82 indicating the region of interest 210. As a result, it is possible for the user to compare the region-of-interest GUI 82 indicating the region of interest 210 in the rotation axis direction of the subject 200, which has been automatically set, with the subject 200 in the X-ray projection image 51 and easily visually determine whether or not the region of interest 210 in the rotation axis direction of the subject 200, which has been automatically set, is a region desired by the user.

In addition, in the X-ray CT apparatus 100 according to the present embodiment, the processor 21 acquires the position of the end part 200a in the rotation axis direction of the subject 200 based on the change in the brightness value of the X-ray projection image 51, as the detection result of the X-ray detector 12, in the rotation axis direction (Z direction) of the subject 200. Moreover, the processor 21 performs the processing of automatically setting the position of the region of interest 210 in the rotation axis direction of the subject 200 based on the acquired position of the end part 200a in the rotation axis direction of the subject 200. As a result, since the position of the region of interest 210 is automatically set by the processor 21 based on the position of the end part 200a, it is possible to more easily set the position of the region of interest 210 based on the position of the end part 200a than a case in which the position of the region of interest 210 is set only by the manual input by the user. In addition, the processor 21 performs the processing of displaying, on the display device 42, the region-of-interest GUI 82 (rotation axis direction region-of-interest GUI) indicating the region of interest 210 in the rotation axis direction of the subject 200 which has been automatically set by the processor 21 based on the change in the brightness value of the X-ray projection image 51 in the rotation axis direction of the subject 200. As a result, it is possible for the user to grasp the position of the region of interest 210 in the rotation axis direction of the subject 200, which has been automatically set by the processor 21 based on the change in the brightness value of the X-ray projection image 51 in the rotation axis direction of the subject 200, by visually recognizing the region-of-interest GUI 82. As a result, it is possible for the user to compare the region-of-interest GUI 82 with the subject 200 in the X-ray projection image 51 and easily visually determine whether or not the position of the region of interest 210 in the rotation axis direction of the subject 200, which has been automatically set based on the change in the brightness value, is the position desired by the user.

Modification Example

It should be noted that the embodiment disclosed this time is an exemplary example in all respects and is not considered to be restrictive. The scope of the present invention is shown by the scope of claims, not the description of the above embodiment, and further includes all changes (modification examples) within the meaning and the scope equivalent to the scope of claims.

For example, in the embodiment described above, the example has been described in which the region of interest 210 in the rotation axis direction of the subject 200 corresponding to the position of the end part 200a in the rotation axis direction of the subject 200 is automatically set by the processor 21 based on the change in the brightness value of the X-ray projection image 51 in the rotation axis direction (Z direction) of the subject 200, but the present invention is not limited to this. In the present invention, as in the modification example shown in FIG. 16, the region of interest 210 in the rotation axis direction of the subject 200 corresponding to the position of the end part 200a in the rotation axis direction of the subject 200 may be automatically set by the processor 21 based on the change in the rotation axis direction of the tomographic image 52. Specifically, in the modification example shown in FIG. 16, the processor 21 detects a tomographic image 52a corresponding to the position of the end part 200a in the rotation axis direction of the subject 200 from among a plurality of constructed tomographic images 52. Moreover, the processor 21 performs the processing of automatically setting the position of the region of interest 210 in the rotation axis direction of the subject 200 based on the position of the end part 200a in the rotation axis direction of the subject 200 corresponding to the tomographic image 52a.

Figure 16:
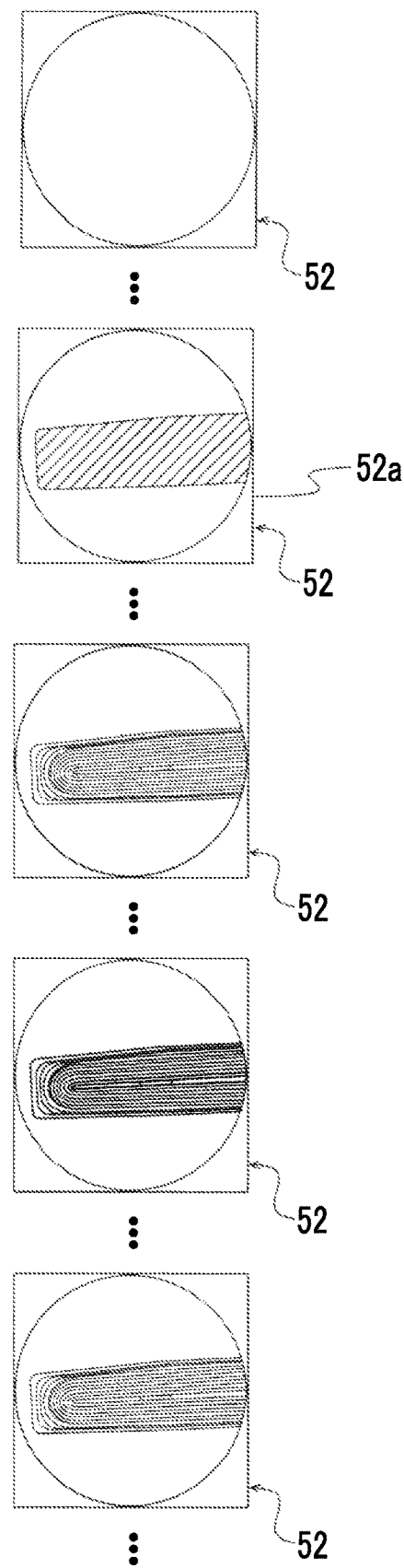
FIG. 16 is a diagram for describing another example of the automatic setting processing of the region of interest based on the X-ray projection image according to a modification example.

In the modification example shown in FIG. 16, the processor 21 performs the processing of acquiring the position of the end part 200a in the rotation axis direction of the subject 200 based on the change in the tomographic image 52, as the detection result of the X-ray detector 12, in the rotation axis direction. Moreover, the processor 21 performs the processing of automatically setting the position of the region of interest 210 in the rotation axis direction of the subject 200 based on the acquired position of the end part 200a in the rotation axis direction of the subject 200. As a result, since the position of the region of interest 210 is automatically set by the processor 21 based on the position of the end part 200a, it is possible to more easily set the position of the region of interest 210 based on the position of the end part 200a than a case in which the position of the region of interest 210 is set only by the manual input by the user. In addition, the processor 21 performs the processing of displaying, on the display device 42, the region-of-interest GUI 82 indicating the region of interest 210 in the rotation axis direction of the subject 200 which has been automatically set by the processor 21 based on the change in the tomographic image 52 in the rotation axis direction. As a result, it is possible for the user to grasp the position of the region of interest 210 in the rotation axis direction of the subject 200, which has been automatically set by the processor 21 based on the change in the tomographic image 52 in the rotation axis direction, by visually recognizing the region-of-interest GUI 82. As a result, it is possible for the user to compare the region-of-interest GUI 82 with the subject 200 in the X-ray projection image 51 and easily visually determine whether or not the position of the region of interest 210 in the rotation axis direction of the subject 200, which has been automatically set based on the change in the tomographic image 52 in the rotation axis direction, is the position desired by the user.

In addition, in the embodiment described above, the example has been described in which, in a case in which the check box 71 (region-of-interest automatic setting GUI) is checked, the processing of automatically setting the region of interest 210 in the rotation axis direction of the subject 200 is executed by the processor 21 simultaneously with the processing of switching to the mode for setting the region of interest 210 for which the region-of-interest reconstruction processing is executed and the Hilbert transformation region 220, but the present invention is not limited to this. In the present invention, the processing of switching to the mode for setting the region of interest and the Hilbert transformation region for which the region-of-interest reconstruction processing is executed and the processing of automatically setting the region of interest in the rotation axis direction of the subject may be performed at different timings. In addition, in the present invention, the GUI for switching to the mode for setting the region of interest and the Hilbert transformation region for which the region-of-interest reconstruction processing is executed and the region-of-interest automatic setting GUI may be different GUIs.

In addition, in the embodiment described above, the example has been described in which, in a case in which the check box 71 (region-of-interest automatic setting GUI) is checked, the processing of automatically setting the region of interest 210 in the rotation axis direction of the subject 200 and the processing of automatically setting the Hilbert transformation region 220 are executed by the processor 21 simultaneously with the processing of switching to the mode for setting the region of interest 210 for which the region-of-interest reconstruction processing is executed and the Hilbert transformation region 220, but the present invention is not limited to this. In the present invention, the processing of automatically setting the region of interest in the rotation axis direction of the subject and the processing of automatically setting the Hilbert transformation region may be performed at different timings. In addition, in the present invention, the region-of-interest automatic setting GUI and the GUI for performing the processing of automatically setting the Hilbert transformation region may be different GUIs. In addition, in the present invention, the automatic setting processing may be performed only on the region of interest in the rotation axis direction of the subject.

In addition, in the embodiment described above, the example has been described in which the processing of displaying, on the display device 42, the region-of-interest GUI 82 (rotation axis direction region-of-interest GUI) in a superimposed manner on the X-ray projection image 51 is performed, but the present invention is limited to this. In the present invention, the rotation axis direction region-of-interest GUI may be displayed in a region that is not superimposed on the tomographic image on the display device.

In addition, in the embodiment described above, the example has been described in which the processor 21 performs the processing of adjusting (manually adjusting) the region of interest 210 in the rotation axis direction (Z direction) of the subject 200 according to the input to the GUI by the input device 41, and also performs the processing of setting (automatically setting) the region of interest 210 in the rotation axis direction (Z direction) of the subject 200 according to the input to the GUI by the input device 41, but the present invention is not limited to this. In the present invention, the processor may only perform any one of the processing of setting (automatically setting) the region of interest in the rotation axis direction (Z direction) of the subject according to the input to the GUI by the input device and the processing of adjusting (manually adjusting) the region of interest in the rotation axis direction (Z direction) of the subject according to the input to the GUI by the input device.

In addition, in the embodiment described above, the example has been described in which the processor 21 performs the processing of adjusting the position and the width of the region of interest 210 in the rotation axis direction (Z direction) of the subject 200 according to the input to the region-of-interest GUI 82 (rotation axis direction region-of-interest GUI) by the input device 41, but the present invention is not limited to this. In the present invention, the processor may be configured to adjust only the position of the region of interest in the rotation axis direction (Z direction) of the subject according to the input to the rotation axis direction region-of-interest GUI by the input device.

In addition, in the embodiment described above, the example has been described in which the processor 21 performs the processing of automatically setting the region of interest 210 in the rotation axis direction (Z direction) of the subject 200 based on the input to the check box 71 (region-of-interest automatic setting GUI) by the input device 41, but the present invention is not limited to this. In the present invention, the processor may simply perform the processing of adjusting the region of interest in the rotation axis direction of the subject according to the input (manual input by the user) to the region-of-interest automatic setting GUI by the input device without performing the processing of automatically setting the region of interest in the rotation axis direction of the subject. In addition, the region of interest in the rotation axis direction of the subject may be set or adjusted by drawing a figure indicating the region of interest in the rotation axis direction of the subject on the X-ray projection image.

In addition, in the embodiment described above, the example has been described in which the region of interest 210 in the direction along the XY plane orthogonal to the rotation axis direction (Z direction) and the region of interest 210 in the rotation axis direction (Z direction) can be adjusted by the region-of-interest GUI 72 and the region-of-interest GUI 82, respectively, but the present invention is not limited to this. In the present invention, the GUI may be able to adjust only the region of interest in the rotation axis direction (Z direction).

In addition, in the embodiment described above, in a case in which the region of the region-of-interest GUI 72 superimposed on the tomographic image 52 is changed, the processor 21 performs the processing of adjusting the Hilbert transformation region 220 such that the transformation region GUI 73 indicating the Hilbert transformation region 220 for the tomographic image 52 is included inside the region-of-interest GUI 72, but the present invention is not limited to this. In the present invention, the Hilbert transformation region may be adjusted separately from changing the region of the region-of-interest GUI.

In addition, in the embodiment described, for convenience of description, the region-of-interest reconstruction processing according to the embodiment of the present invention has been described by using a flow-driven type flowchart that performs processing in order along the processing flow, but the present invention is not limited to this. In the present invention, the processing operations in the region-of-interest reconstruction processing may be performed by the processing of an event-driven type that executes processing on an event-by-event basis. In this case, the processing operations in the region-of-interest reconstruction processing may be performed in a completely event-driven type, or may be performed in combination of an event-driven type and a flow-driven type.

Aspects

It will be understood by those skilled in the art that the exemplary embodiment described above is a specific example of the below aspects.

Item 1

An X-ray CT apparatus including an X-ray irradiator configured to emit X-rays, an X-ray detector configured to detect the X-rays emitted from the X-ray irradiator and transmitted through a subject, and a processor configured to perform tomographic image construction processing of constructing a tomographic image of the subject based on projection data acquired by irradiating the subject with the X-rays from a plurality of angles while rotating the subject, and perform region-of-interest reconstruction processing of reconstructing the tomographic image of the subject in a region of interest by executing Hilbert transformation, in which the processor is configured to display, on a display device, an X-ray projection image based on the projection data, and perform processing of displaying a GUI, which is a graphical user interface for setting or adjusting the region of interest in a rotation axis direction of the subject for which the tomographic image is reconstructed, in the region-of-interest reconstruction processing.

Item 2

The X-ray CT apparatus according to item 1, in which the GUI includes a rotation axis direction region-of-interest GUI indicating the region of interest in the rotation axis direction of the subject, and the processor is configured to perform processing of displaying, on the display device, the rotation axis direction region-of-interest GUI in a superimposed manner on the X-ray projection image.

Item 3

The X-ray CT apparatus according to item 2, further including an input device for performing input to the GUI, in which the processor is configured to perform processing of setting or adjusting the region of interest in the rotation axis direction of the subject according to the input to the GUI by the input device.

Item 4

The X-ray CT apparatus according to item 3, in which the processor is configured to perform processing of adjusting at least a position of the region of interest in the rotation axis direction of the subject according to the input to the rotation axis direction region-of-interest GUI by the input device.

Item 5

The X-ray CT apparatus according to item 1, in which the processor is configured to perform processing of automatically setting the region of interest in the rotation axis direction of the subject.

Item 6

The X-ray CT apparatus according to item 5, in which the GUI includes a region-of-interest automatic setting GUI for the processor to automatically set the region of interest in the rotation axis direction of the subject, and the processor is configured to perform processing of automatically setting the region of interest in the rotation axis direction of the subject based on input to the region-of-interest automatic setting GUI.

Item 7

The X-ray CT apparatus according to item 5, in which the processor is configured to perform processing of automatically setting the region of interest in the rotation axis direction of the subject corresponding to a size in the rotation axis direction of the subject based on a detection result of the X-ray detector.

Item 8

The X-ray CT apparatus according to item 7, in which the processor is configured to acquire a position of an end part in the rotation axis direction of the subject based on a change in a brightness value of the X-ray projection image, as the detection result of the X-ray detector, in the rotation axis direction of the subject, and perform processing of automatically setting a position of the region of interest in the rotation axis direction of the subject based on the acquired position of the end part in the rotation axis direction of the subject.

Item 9

The X-ray CT apparatus according to item 7, in which the processor is configured to acquire a position of an end part in the rotation axis direction of the subject based on a change in the tomographic image, as the detection result of the X-ray detector, in the rotation axis direction, and perform processing of automatically setting a position of the region of interest in the rotation axis direction of the subject based on the acquired position of the end part in the rotation axis direction of the subject.

Item 10

The X-ray CT apparatus according to any one of items to 9, in which the GUI includes a rotation axis direction region-of-interest GUI indicating the region of interest in the rotation axis direction of the subject, and the processor is configured to perform processing of displaying, on the display device, the rotation axis direction region-of-interest GUI which has been automatically set by the processor.

Item 11

A reconstruction method of a tomographic image, the method including a tomographic image construction processing step of performing tomographic image construction processing of constructing a tomographic image of a subject based on projection data acquired by irradiating the subject with X-rays from a plurality of angles, a projection image display step of displaying an X-ray projection image based on the projection data, a GUI display step of displaying a GUI, which is a graphical user interface for setting or adjusting a region of interest in a rotation axis direction of the subject for which the tomographic image is reconstructed, in region-of-interest reconstruction processing of reconstructing the tomographic image of the subject in the region of interest by executing Hilbert transformation, and a region-of-interest reconstruction processing step of performing the region-of-interest reconstruction processing based on the region of interest in the rotation axis direction of the subject which has been set or adjusted by using the GUI.

What is claimed is:

1. An X-ray CT apparatus comprising:
   an X-ray irradiator configured to emit X-rays;
   an X-ray detector configured to detect the X-rays emitted from the X-ray irradiator and transmitted through a subject; and
   a processor configured to perform tomographic image construction processing of constructing a tomographic image of the subject based on projection data acquired by irradiating the subject with the X-rays from a plurality of angles while rotating the subject, and perform region-of-interest reconstruction processing of reconstructing the tomographic image of the subject in a region of interest by executing Hilbert transformation,
   wherein the processor is configured to display, on a display device, an X-ray projection image based on the projection data, and perform processing of displaying a GUI, which is a graphical user interface for setting or adjusting the region of interest in a rotation axis direction of the subject for which the tomographic image is reconstructed, in the region-of-interest reconstruction processing.

2. The X-ray CT apparatus according to claim 1,
   wherein the GUI includes a rotation axis direction region-of-interest GUI indicating the region of interest in the rotation axis direction of the subject, and
   the processor is configured to perform processing of displaying, on the display device, the rotation axis direction region-of-interest GUI in a superimposed manner on the X-ray projection image.

3. The X-ray CT apparatus according to claim 2, further comprising:
   an input device for performing input to the GUI,
   wherein the processor is configured to perform processing of setting or adjusting the region of interest in the rotation axis direction of the subject according to the input to the GUI by the input device.

4. The X-ray CT apparatus according to claim 3,
   wherein the processor is configured to perform processing of adjusting at least a position of the region of interest in the rotation axis direction of the subject according to input to the rotation axis direction region-of-interest GUI by the input device.

5. The X-ray CT apparatus according to claim 1,
   wherein the processor is configured to perform processing of automatically setting the region of interest in the rotation axis direction of the subject.

6. The X-ray CT apparatus according to claim 5,
wherein the GUI includes a region-of-interest automatic setting GUI for the processor to automatically set the region of interest in the rotation axis direction of the subject, and
the processor is configured to perform processing of automatically setting the region of interest in the rotation axis direction of the subject based on input to the region-of-interest automatic setting GUI.

7. The X-ray CT apparatus according to claim 5,
wherein the processor is configured to perform processing of automatically setting the region of interest in the rotation axis direction of the subject corresponding to a size in the rotation axis direction of the subject based on a detection result of the X-ray detector.

8. The X-ray CT apparatus according to claim 7,
wherein the processor is configured to
acquire a position of an end part in the rotation axis direction of the subject based on a change in a brightness value of the X-ray projection image, as the detection result of the X-ray detector, in the rotation axis direction of the subject, and
perform processing of automatically setting a position of the region of interest in the rotation axis direction of the subject based on the acquired position of the end part in the rotation axis direction of the subject.

9. The X-ray CT apparatus according to claim 7,
wherein the processor is configured to
acquire a position of an end part in the rotation axis direction of the subject based on a change in the tomographic image, as the detection result of the X-ray detector, in the rotation axis direction, and
perform processing of automatically setting a position of the region of interest in the rotation axis direction of the subject based on the acquired position of the end part in the rotation axis direction of the subject.

10. The X-ray CT apparatus according to claim 5,
wherein the GUI includes a rotation axis direction region-of-interest GUI indicating the region of interest in the rotation axis direction of the subject, and
the processor is configured to perform processing of displaying, on the display device, the rotation axis direction region-of-interest GUI which has been automatically set by the processor.

11. A reconstruction method of a tomographic image, the method comprising:
a tomographic image construction processing step of performing tomographic image construction processing of constructing a tomographic image of a subject based on projection data acquired by irradiating the subject with X-rays from a plurality of angles;
a projection image display step of displaying an X-ray projection image based on the projection data;
a GUI display step of displaying a GUI, which is a graphical user interface for setting or adjusting a region of interest in a rotation axis direction of the subject for which the tomographic image is reconstructed, in region-of-interest reconstruction processing of reconstructing the tomographic image of the subject in the region of interest by executing Hilbert transformation; and
a region-of-interest reconstruction processing step of performing the region-of-interest reconstruction processing based on the region of interest in the rotation axis direction of the subject which has been set or adjusted by using the GUI.

* * * * *